US011532135B2

(12) United States Patent
Geri et al.

(10) Patent No.: US 11,532,135 B2
(45) Date of Patent: Dec. 20, 2022

(54) DUAL MODE AUGMENTED REALITY SURGICAL SYSTEM AND METHOD

(71) Applicant: Surgical Theater, Inc., Mayfield Village, OH (US)

(72) Inventors: Alon Yakob Geri, Beachwood, OH (US); Mordechai Avisar, Highland Heights, OH (US)

(73) Assignee: SURGICAL THEATER, INC., Los Angeles, CA (US)

( * ) Notice: Subject to any disclaimer, the term of this patent is extended or adjusted under 35 U.S.C. 154(b) by 190 days.

(21) Appl. No.: 17/114,333

(22) Filed: Dec. 7, 2020

(65) Prior Publication Data

US 2021/0090344 A1 Mar. 25, 2021

Related U.S. Application Data

(63) Continuation of application No. 15/699,686, filed on Sep. 8, 2017, now Pat. No. 10,861,236.

(51) Int. Cl.
*G06T 19/00* (2011.01)
*G06T 7/73* (2017.01)
(Continued)

(52) U.S. Cl.
CPC ............ *G06T 19/006* (2013.01); *A61B 34/20* (2016.02); *A61B 90/36* (2016.02);
(Continued)

(58) Field of Classification Search
None
See application file for complete search history.

(56) References Cited

U.S. PATENT DOCUMENTS 5,595,703 A 1/1997 Swaelens et al.
5,768,134 A 6/1998 Swaelens et al.
(Continued)

FOREIGN PATENT DOCUMENTS

CN 1720561 A 1/2006
CN 1973780 A 6/2007
(Continued)

OTHER PUBLICATIONS

Montgomery, K. et al; Studies in Health Technology and Informatics; "Spring: A General Framework for Collaborative, Real-time Surgical Simulation"; 2002, vol. 85, pp. 296-303.
(Continued)

*Primary Examiner* — Steven Z Elbinger
(74) *Attorney, Agent, or Firm* — Bodi Law LLC

(57) ABSTRACT

A dual mode augmented reality surgical system configured to operate in both a tracking and a non-tracking mode includes a head mounted display configured to provide an optical view of a patient and to inject received data content over top of the optical view to form an augmented reality view of the patient, and comprising internal tracking means configured to determine a surgeon's position as well as angle and direction of view relative to the patient. The system further includes an augmented reality computing system comprising one or more processors, one or more computer-readable tangible storage devices, and program instructions stored on at least one of the one or more storage devices for execution by at least one of the one or more processors.

20 Claims, 10 Drawing Sheets

(51) Int. Cl.
| | |
|---|---|
| G06T 15/20 | (2011.01) |
| G02B 27/01 | (2006.01) |
| A61B 90/00 | (2016.01) |
| A61B 34/20 | (2016.01) |
| G06F 3/01 | (2006.01) |
| G06F 1/16 | (2006.01) |
| G16H 40/63 | (2018.01) |
| G16H 20/40 | (2018.01) |
| G16H 50/50 | (2018.01) |
| G16H 30/20 | (2018.01) |
| G16H 10/60 | (2018.01) |
| A61B 90/50 | (2016.01) |
| A61B 34/10 | (2016.01) |

(52) U.S. Cl.
CPC ......... *G02B 27/0172* (2013.01); *G06F 1/163* (2013.01); *G06F 3/011* (2013.01); *G06F 3/012* (2013.01); *G06T 7/73* (2017.01); *G06T 15/20* (2013.01); *G06T 19/003* (2013.01); *G16H 10/60* (2018.01); *G16H 20/40* (2018.01); *G16H 30/20* (2018.01); *G16H 40/63* (2018.01); *G16H 50/50* (2018.01); *A61B 2034/105* (2016.02); *A61B 2034/2055* (2016.02); *A61B 2034/2068* (2016.02); *A61B 2034/2074* (2016.02); *A61B 2090/365* (2016.02); *A61B 2090/372* (2016.02); *A61B 2090/502* (2016.02); *G02B 2027/014* (2013.01); *G06T 2200/24* (2013.01); *G06T 2207/30196* (2013.01); *G06T 2207/30204* (2013.01)

(56) References Cited

U.S. PATENT DOCUMENTS

| | | |
|---|---|---|
| 5,826,206 A | 10/1998 | Nemeth |
| 6,037,927 A | 3/2000 | Rosenberg |
| 6,113,395 A | 9/2000 | Hon |
| 6,847,336 B1 | 1/2005 | Lemelson |
| 6,857,878 B1 | 2/2005 | Chosack et al. |
| 6,863,536 B1 | 3/2005 | Fisher et al. |
| 6,939,138 B2 | 9/2005 | Chosack et al. |
| 7,101,383 B1 | 9/2006 | Van Ess |
| 7,261,565 B2 | 8/2007 | Chosack et al. |
| 7,616,730 B2 | 11/2009 | Flohr |
| 8,311,791 B1 | 11/2012 | Avisar |
| 8,504,136 B1 | 8/2013 | Sun |
| 9,547,940 B1 * | 1/2017 | Sun ..................... A61B 1/044 |
| 9,788,905 B2 | 10/2017 | Avisar |
| 10,056,012 B2 | 8/2018 | Geri et al. |
| 2001/0046935 A1 | 11/2001 | Okamura |
| 2002/0059284 A1 | 5/2002 | Bronstein et al. |
| 2004/0253572 A1 | 12/2004 | Chosack et al. |
| 2005/0032028 A1 | 2/2005 | Chosack et al. |
| 2006/0036167 A1 | 2/2006 | Shina |
| 2006/0082542 A1 | 4/2006 | Morita et al. |
| 2006/0085175 A1 | 4/2006 | Hartlep et al. |
| 2006/0281971 A1 | 12/2006 | Sauer |
| 2007/0129626 A1 | 6/2007 | Mahesh et al. |
| 2007/0134637 A1 | 6/2007 | Bronstein et al. |
| 2007/0141543 A1 | 6/2007 | Grund-Pedersen |
| 2007/0248261 A1 | 10/2007 | Zhou et al. |
| 2009/0018808 A1 | 1/2009 | Bronstein et al. |
| 2009/0187393 A1 | 7/2009 | Van Lierde et al. |
| 2009/0311655 A1 | 12/2009 | Karkanias et al. |
| 2010/0009314 A1 | 1/2010 | Tardieu et al. |
| 2010/0092904 A1 | 4/2010 | Esposti et al. |
| 2010/0161076 A1 | 6/2010 | Pallari |
| 2010/0178644 A1 | 7/2010 | Meglan et al. |
| 2010/0191088 A1 | 7/2010 | Anderson et al. |
| 2010/0217336 A1 | 8/2010 | Crawford et al. |
| 2010/0305928 A1 | 12/2010 | Cohen et al. |
| 2011/0236868 A1 | 9/2011 | Bronstein et al. |
| 2011/0238395 A1 | 9/2011 | Kubota et al. |
| 2012/0058457 A1 | 3/2012 | Savitsky |
| 2013/0047103 A1 | 2/2013 | Avisar |
| 2013/0172906 A1 | 7/2013 | Olson |
| 2013/0267838 A1 | 10/2013 | Fronk |
| 2014/0171959 A1 | 6/2014 | Yacono |
| 2014/0176661 A1 | 6/2014 | Smurro et al. |
| 2014/0275760 A1 | 9/2014 | Lee |
| 2014/0303491 A1 * | 10/2014 | Shekhar ............. A61B 1/00193 600/424 |
| 2015/0248793 A1 | 9/2015 | Abovitz et al. |
| 2016/0191887 A1 * | 6/2016 | Casas ................... H04N 13/111 348/47 |
| 2016/0225192 A1 * | 8/2016 | Jones ...................... G06F 3/011 |
| 2018/0092698 A1 * | 4/2018 | Chopra ................. A61B 90/39 |
| 2019/0046276 A1 * | 2/2019 | Inglese ................. A61B 34/20 |

FOREIGN PATENT DOCUMENTS

| | | |
|---|---|---|
| CN | 102354345 A | 2/2012 |
| EP | 1 395 194 A1 | 3/2004 |
| EP | 3 146 715 A1 | 3/2017 |
| EP | 3 280 344 A2 | 2/2018 |
| JP | 2006509238 A | 3/2006 |
| JP | 2006223374 | 8/2006 |
| JP | 2010131047 | 6/2010 |
| JP | 2014522248 | 9/2014 |
| JP | 2014525764 | 10/2014 |
| WO | WO9610949 | 4/1996 |
| WO | WO 02/100284 A1 | 12/2002 |
| WO | 2004029908 A1 | 4/2004 |
| WO | 2004051603 A1 | 6/2004 |
| WO | WO2004051603 | 6/2004 |
| WO | WO 2008/076079 | 6/2008 |
| WO | 2009059716 A1 | 5/2009 |
| WO | WO2009059716 | 5/2009 |
| WO | 2009094621 A2 | 7/2009 |
| WO | 2010030523 A1 | 3/2010 |
| WO | WO2010106532 A1 | 9/2010 |
| WO | 2010132606 A1 | 11/2010 |
| WO | 2012/033739 A1 | 3/2012 |
| WO | 2012135653 A1 | 10/2012 |
| WO | 2013177520 A1 | 11/2013 |
| WO | WO 2015/008470 A2 | 1/2015 |
| WO | 2015154069 A1 | 10/2015 |

OTHER PUBLICATIONS

Qin, J. et al; Studies in Health Technology and Informatics; "An Adaptive Framework Using Cluster-Based Hybrid Architecture for Enhancing Collaboration in Surgical Simulation"; 2007, vol. 125, pp. 367-372.

Joanna Leng; Scientific Examples of Virtual Reality and Visualization Applications; Manchester Research Center for Computational Science; Mar. 2001; part "Surgical Simulation."

J Neurosurg vol. 93; Relevant Pages: pp. 355-369 and Figures 3, 4, 6 and 8; Date of Issuance: Aug. 31, 2000; Title of Article: "Simulation of the surgical manipulation involved in clipping a basilar artery aneurysm: concepts of virtual clipping"; Author and Publisher: Toru Koyama, M.D. et al.; Department of Neurosurgery, Shinshu University School of Medicine Matsumoto, Japan.

Bornik A et al: "Computer Aided Liver Surgery Planni ng: An Augmented Reality Approach" Visual Communications and Image Processing; vol. 5029, Feb. 15, 2003, pp. 395-406.

Reitinger, et al: "Liver Surgery Planning Using Virtual Reality"; Virtual and Augmented Reality Supported Similators; IEEE Computer Society; Nov./Dec. 2006.

* cited by examiner

DUAL MODE AUGMENTED REALITY SURGICAL SYSTEM AND METHOD

CROSS-REFERENCES TO RELATED APPLICATIONS

This application is a continuation of U.S. patent application Ser. No. 15/699,686, U.S. Pat. No. 10,861,263, filed on Sep. 8, 2017 and incorporated herein by reference.

BACKGROUND

Surgical procedures may often be complex and time sensitive and vary in scope from one patient to another. For example, in the case of an aneurysm repair, the point of repair may vary in terms or procedural requirements depending on the exact location, size, and so on. Therefore, the efficiency of the procedure is highly critical and detailed planning based on the patient specific local geometry and physical properties of the area on which surgery is being performed is fundamental. To achieve a new level of pre-surgery preparation, 3D CT and MRI images are being increasingly utilized. However, those images offer only minor benefits, standing alone, for surgery rehearsal. Moreover, existing techniques for studying a patient's specific anatomy prior to or during surgery may be invasive to the patient.

A surgery rehearsal and preparation tool previously described in U.S. Pat. No. 8,311,791, incorporated herein by reference, has been developed to convert static medical images into dynamic and interactive multi-dimensional full spherical virtual reality, six (6) degrees of freedom models ("MD6DM") that can be used by physicians to simulate medical procedures in real time.

The MD6DM provides a graphical simulation environment which enables the physician to experience, plan, perform, and navigate the intervention in full spherical virtual reality environment. In particular, the MD6DM gives the surgeon the capability to navigate using a unique multidimensional model, built from traditional 2 dimensional patient medical scans, that gives spherical virtual reality 6 degrees of freedom (i.e. linear; x, y, z, and angular, yaw, pitch, roll) in the entire volumetric spherical virtual reality model.

The MD6DM is built from the patient's own data set of medical images including CT, MRI, DTI etc., and is patient specific. A representative brain model, such as Atlas data, can be integrated to create a partially patient specific model if the surgeon so desires. The model gives a 360° spherical view from any point on the MD6DM. Using the MD6DM, the viewer is positioned virtually inside the anatomy and can look and observe both anatomical and pathological structures as if he were standing inside the patient's body. The viewer can look up, down, over the shoulders etc., and will see native structures in relation to each other, exactly as they are found in the patient. Spatial relationships between internal structures are preserved, and can be appreciated using the MD6DM.

The algorithm of the MD6DM takes the medical image information and builds it into a spherical model, a complete continuous real time model that can be viewed from any angle while "flying" inside the anatomical structure. In particular, after the CT, MRI, etc. takes a real organism and deconstructs it into hundreds of thin slices built from thousands of points, the MD6DM reverts it to a 3D model by representing a 360° view of each of those points from both the inside and outside.

In one example, a physician may want to leverage the information available in the MD6DM and use it during an actual surgery procedure inside an operating room (OR). However, a surgeon may already be using a microscope or an endoscope in the operating room during a procedure. Thus, it may be inefficient, distracting, and time consuming for the surgeon to take his eyes off the microscope or endoscope to look at the MD6DM or other types of patient scans or data. In addition, including additional equipment and systems for viewing patient scans and models such as MD6DM in an already crowded operating room may not be practical or possible.

An Augmented Reality Surgical Navigation System was previously described in PCT Patent Application no. PCT/US2016/056727, incorporated herein by reference, has been developed to enable a physician to view a virtual patient model in real time over top of the actual physical patient, that tracks the physical patient, in an augmented reality view. However, tracking a patient view and aligning the virtual model in an augmented reality view may rely on external tracking mechanisms in the hospital room which may not always be available to the system. In particular, such external tracking mechanisms may be expensive, time consuming, and impractical to implement. In addition, a physician may desire additional flexibility and the ability to leverage additional information available from other systems during a surgical procedure while working within a room that may have limited space and maneuverability.

In addition, a physician may need to rely on information from several sources during a surgery in order to be effective. However, it may be critical for the surgeon to stay focused on the patient during surgery and it may be inconvenient, difficult, or impractical to look away from a patient in order to focus on such other information during the surgery.

SUMMARY

An augmented reality surgical system includes a head mounted display configured to provide an optical view of a patient and to inject received data content over top of the optical view to form an augmented reality view of the patient. The system further includes an augmented reality computing system comprising one or more processors, one or more computer-readable tangible storage devices, and program instructions stored on at least one of the one or more storage devices for execution by at least one of the one or more processors. The program instructions include first program instructions for receiving a plurality of data content from a plurality of data sources; second program instructions for integrating the plurality of data content according to a defined layout and communicating the integrated plurality of data content to the head mounted display to form an augmented reality view of the patient; third program instructions for receiving interaction control data indicative of a request interact with the plurality of data content; and fourth program instructions for manipulating the augmented reality view of the patient in real-time, based on the received interaction control data, by updating the integrated plurality of data content and communicating the updated integrated plurality of data content to the head mounted display.

A computer program product includes one or more computer-readable tangible storage devices, and program instructions stored on at least one of the one or more storage devices. The program instructions include first program instructions for receiving a plurality of data content from a plurality of data sources; second program instructions for integrating the plurality of data content according to a defined layout and communicating the integrated plurality of data content to a head mounted display to form an augmented reality view of the patient; third program instructions for receiving interaction control data indicative of a request interact with the plurality of data content; and fourth program instructions for manipulating the augmented reality view of the patient in real-time, based on the received interaction control data, by updating the integrated plurality of data content and communicating the updated integrated plurality of data content to the head mounted display.

An augmented reality surgical method includes the steps of receiving a plurality of data content from a plurality of data sources; integrating the plurality of data content according to a defined layout and communicating the integrated plurality of data content to a head mounted display to form an augmented reality view of a patient; receiving interaction control data indicative of a request interact with the plurality of data content; and manipulating the augmented reality view of the patient in real-time, based on the received interaction control data, by updating the integrated plurality of data content and communicating the updated integrated plurality of data content to the head mounted display.

A dual mode augmented reality surgical system configured to operate in both a tracking mode and a non-tracking mode includes a head mounted display configured to provide an optical view of a patient and to inject received data content over top of the optical view to form an augmented reality view of the patient, and comprising internal tracking means configured to determine a surgeon's position as well as angle and direction of view relative to the patient. The system further includes an augmented reality computing system comprising one or more processors, one or more computer-readable tangible storage devices, and program instructions stored on at least one of the one or more storage devices for execution by at least one of the one or more processors. The program instructions include: first program instructions for receiving a plurality of data content from a plurality of data sources; second program instructions for integrating the plurality of data content according to a defined layout and communicating the integrated plurality of data content to the head mounted display to form an augmented reality view of the patient; third program instructions for receiving interaction control data indicative of a request interact with the plurality of data content; fourth program instructions for manipulating the augmented reality view of the patient in real-time, based on the received interaction control data, by updating the integrated plurality of data content and communicating the updated integrated plurality of data content to the head mounted display; and fifth program instructions for receiving tracking information from the tracking means, while the augmented reality surgical system is operating in a tracking mode, and for automatically manipulating the augmented reality view of the patient in real-time, based on the received tracking information, by updating the integrated plurality of data content and communicating the updated integrated plurality of data content to the head mounted display Also provided are additional example embodiments, some, but not all of which, are described herein below in more detail

BRIEF DESCRIPTION OF THE DRAWINGS

The patent or application file contains at least one photograph executed in black and white. Copies of this patent or patent application publication with black and white photograph drawings will be provided by the Office upon request and payment of the necessary fee. In the accompanying drawings, structures are illustrated that, together with the detailed description provided below, describe exemplary embodiments of the claimed invention. Like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

DETAILED DESCRIPTION OF THE EXAMPLE EMBODIMENTS

Figure 1:
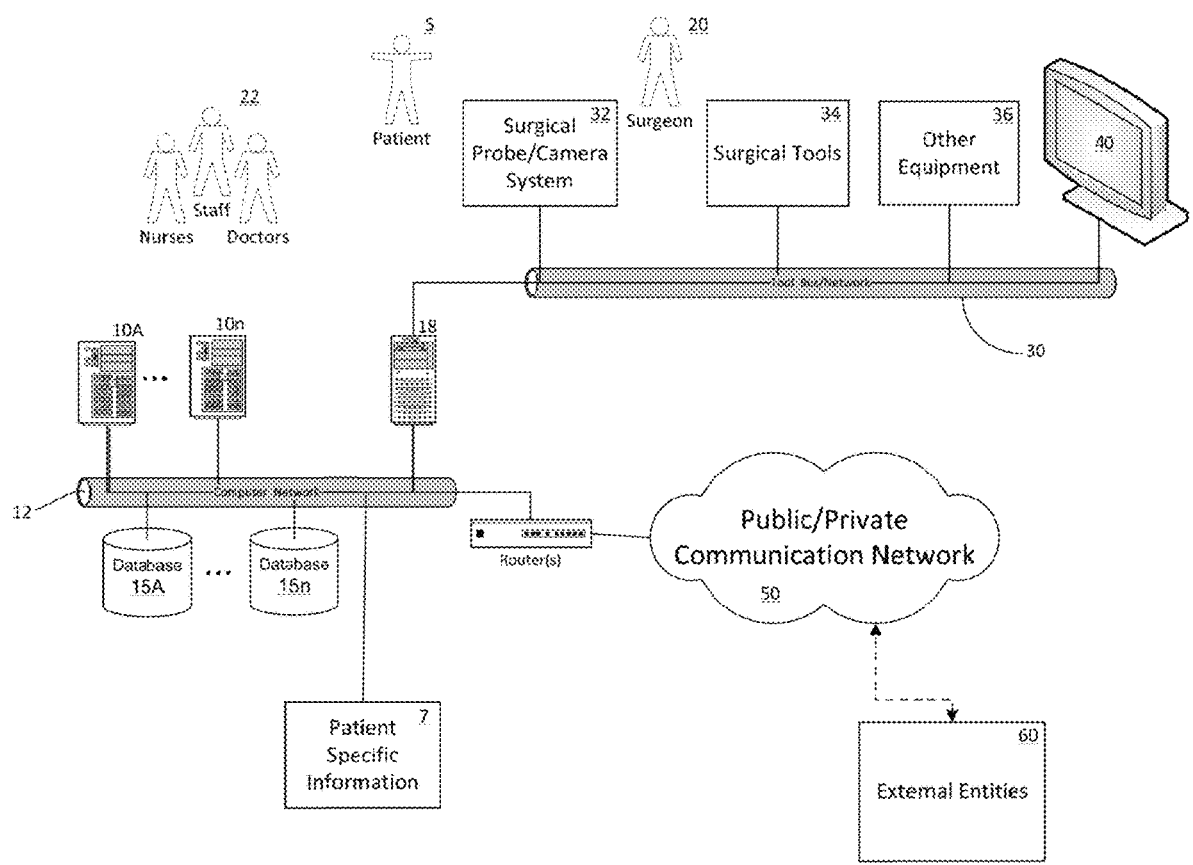
FIG. 1 illustrates a block diagram showing an example system structure and interfaces for utilizing an example SNAP system that can be used with the improvements disclosed herein.

The following acronyms and definitions will aid in understanding the detailed description:

AR—Augmented Reality—A live view of a physical, real-world environment whose elements have been enhanced by computer generated sensory elements such as sound, video, or graphics.

VR—Virtual Reality—A 3 Dimensional computer generated environment which can be explored and interacted with by a person in varying degrees.

HMD—Head Mounted Display (FIG. 9) refers to a headset which can be used in AR or VR environments. It may be wired or wireless. It may also include one or more add-ons such as headphones, microphone, HD camera, infrared camera, hand trackers, positional trackers etc.

Optical View—The pass-through view observed through an AR HMD before any data content is injected, equivalent to same view that would be observed without the AR HMD.

Controller—A device which may include buttons and a direction controller. It may be wired or wireless. Examples of this device are Xbox gamepad, PlayStation gamepad, Oculus touch, etc.

Segmentation—The process of partitioning a digital image into multiple segments (sets of pixels). The goal of segmentation is to simplify and/or change the representation of an image into something that is more meaningful and easier to analyze.

Clipping—The process of removing layers (one pre-set thickness at a time) of modeled anatomy perpendicular to the angle of view in order to reveal internal structures "slice by slice". Layers are removed in the lateral/distal to the medial/proximal direction.

SNAP Case—A SNAP case refers to a 3D texture or 3D objects created using one or more scans of a patient (CT, MR, fMR, DTI, etc.) in DICOM file format. It also includes different presets of segmentation for filtering specific ranges and coloring others in the 3D texture. It may also include 3D objects placed in the scene including 3D shapes to mark specific points or anatomy of interest, 3D Labels, 3D Measurement markers, 3D Arrows for guidance, and 3D surgical tools. Surgical tools and devices have been modeled for education and patient specific rehearsal, particularly for appropriately sizing aneurysm clips.

Scene—Refers to the 3D virtual space, which includes the 3D texture and the 3D objects in it.

Add On Sensors—Devices that allows receiving more information from the real environment in order to enhance the virtual experience. For example—Microsoft Kinect, Leap Motion.

MD6DM—Multi Dimension full spherical virtual reality, 6 Degrees of Freedom Model. It provides a graphical simulation environment which enables the physician to experience, plan, perform, and navigate the intervention in full spherical virtual reality environment.

The disclosed system is implemented on a modeling system such as the example surgical graphical tool (SNAP) which integrates with operating room technology to provide advanced 3D capabilities and augmented reality, allowing surgeons to enhance their surgery performance and prepare in advance. The SNAP tool provides neurosurgeons with unique virtual-reality guidance to determine the safest and most efficient pathway to remove cerebral tumors and treat vascular anomalies, for example, among other uses.

The SNAP tool imports the 3D planning of craniotomy, head position, path approaches to the pathology, for example for Keyhole and other minimally invasive techniques. The SNAP allow the surgeon to see in advance the expected surgeon eye view.

With the SNAP tool, surgeons can execute their surgery plan while in the operating room utilizing a particular patient's actual CT/MRI (and other) scans, allowing enhanced accuracy and efficiency. SNAP also provides innovative features that allow surgeons to see behind arteries and other critical structures, in a rotatable 3D format that can be modified to make the images more useful to the surgeon. For example, SNAP provides the ability to rotate images or make the semi-transparent, to aid the surgeon in visualizing the operation. SNAP makes use of advanced imaging technology that allows a surgeon to perform a real-life "fly through" of a "patient-specific" surgery. The tool provides preparation support outside the operating room and can also be utilized to take the pre-planned pathway into the operating room itself to be used by the surgeon (and his staff) during a procedure.

The SNAP obtains the tracing coordinates of surgery tools, navigation probe, microscope focal point etc. by either connecting to OR intra-operative tracing navigation systems. The SNAP provides 3D navigation model that slows enhanced situational awareness. SNAP can receive image or tracking/navigation information from any of these surgery tools that are configured to collect such information, and such information can be used by the SNAP system to cause the high-resolution image displayed to the surgeon to correspond to the received information. For example, the SNAP image might track the location of the tool in the displayed image, or update the image based on visual information provided by the tool, for example.

SNAP proximity warning systems operates in a similar way that Ground Proximity Warning System (GPWS) and An Airborne Collision Avoidance System (ACAS), Terrain Collision Avoidance System (TCAS) and other similar systems in airplanes which indicate and warns the air crew from proximity and/maneuver that may cause a proximity to the ground and other obstacles. SNAP proximity warning systems operates includes the following main stages:

The SNAP proximity warning systems can automatically mark anatomical structure that the surgeons need to avoid. Such anatomical structure may include fiber track, nerves, vessels, arteries etc.—The SNAP proximity warning systems allows a manual placement of Markets within the 3D or 2D navigation scene. Those Markets can either mark obstacles and anatomical structure to avoid or mark a Target that surgeon will navigate to. Every Marker that is being placed can be labeled, have a specific color, specific shape etc.—The indication of the warning of the SNAP proximity warning systems can be visual (for example changes in color), vocal (sound) and others.

The SNAP can allow creating a Trajectory. By marketing Entry point and then associating this entry point with the above Marker/target, the SNAP creates a Trajectory that allows to navigate from the Entry point to the Target. —The SNAP Path planner allows surgeons to connect several, Markers, Target and Entry points and do create Path. Multiple Paths can be created. Path can be a desired route to follow or a Path to avoid.

The SNAP provides visual graphic guidance to the surgeon. As far as the surgeon maintains his movements within the guided markers, the he will get accurately from point A to point B (from Entry point to Target). The tool provides institutions (e.g., hospitals) and their respective surgeons with the opportunity to reduce surgical errors, decrease the amount of surgical waste and related costs, reduce operating room time, and minimize the high-risk nature of the procedures. The tool provides for an opportunity to maintain high quality in neurosurgery training, and for taking the Education outside of the operating room: Halstedian training for surgery skills depends on a large volume, a wide variety of cases, and almost endless resident's time in the hospital. Recent developments have forced a rethinking of the Halstedian system. The recent constellation of pressures on Halstedian system includes; restricted work hours, increased public scrutiny, and reduction in operative experience.

Rehearsal using the tool can reduce the need for follow-up procedures and adjustments. For example, the tool, when used for aneurism surgery, using the tool can reduce the need for adjusting or replacing an aneurism clip. Adjustments and replacement of the clip can typically result in extended temporary occlusion and overall longer procedure time. This may increase overall procedure risk.

As will be appreciated by one of skill in the art, the example embodiments disclosed herein may be actualized as, or may generally utilize, a method, system, computer program product, or a combination of the foregoing. Accordingly, any of the embodiments may take the form of an entirely hardware embodiment, an entirely software embodiment (including firmware, resident software, microcode, etc.) for execution on hardware, or an embodiment combining software and hardware aspects that may generally be referred to herein as a "system." Furthermore, any of the embodiments may take the form of a computer program product on a computer-usable storage medium having computer-usable program code embodied in the medium.

For example, the features disclosed herein can be implemented using a networked computer system 1 provided in a hospital setting (such as in an operating room), as shown in FIG. 1. This system can be provided in the surgical setting, where a surgeon 20 operates on a patient 5 supported by various surgical staff 22. Such a system 1 integrates one or more servers (e.g., PCs) 10A-10n accessing data from one or more databases 15A-15n that are networked together using a computer network 12. The system will execute proprietary software provided to implement the functions and other features described herein. One or more computers 20 can be used to interface with various surgical tools such as a surgical probe/camera 32, other surgical tools 34, and/or other equipment 36 connected to the computer(s) 20 using one or more computer busses or networks 30 as an interface between the computer 18 and the tools. Note that in some situations, all of the computers 18, servers 10, and databases 15 might be housed in a single server platform.

The system is connected to a high-resolution 3D display 40 on which the surgeon can monitor the operation and activity of the various tools 32, 34, and 36. In some cases, a display may not have 3D capability. Furthermore, the Example Head Mounted Display (HMD) described below can be utilized to provide realistic images to the surgeon and/or his/her assistants. One or more such displays may be provided remotely from the operation location, such as through a connection via a communication network such as the Internet.

The system is configured with patient specific parameters 7 which include imaging details of the patient including images prepare from the patient's available CT and MRI images that were previously obtained, and other information that concerns the simulated models such as patient age, gender, and so on (some or all of which may be obtained from external entities, such as medical databases, laboratories, or other sources, for example). The system utilizes tissue information parameters obtained from a system database(s) that describe tissue and organ features. The system can be configured to interact with one or more external entities 60 via a communication network 50, such as the Internet, where desired.

Any suitable computer usable (computer readable) medium may be utilized for storing the software for execution on one or more of the computers for realizing the disclosed processes and for storing the disclosed data and information. The computer usable or computer readable medium may be, for example but not limited to, an electronic, magnetic, optical, electromagnetic, infrared, or semiconductor system, apparatus, device, or propagation medium. More specific examples (a non-exhaustive list) of the computer readable medium would include the following: an electrical connection having one or more wires; a tangible medium such as a portable computer diskette, a hard disk, a random access memory (RAM), a read-only memory (ROM), an erasable programmable read-only memory (EPROM or Flash memory), a compact disc read-only memory (CDROM), or other tangible optical or magnetic storage device; or transmission media such as those supporting the Internet or an intranet. Note that the computer usable or computer readable medium could even include another medium from which the program can be electronically captured, via, for instance, optical or magnetic scanning for example, then compiled, interpreted, or otherwise processed in a suitable manner, if necessary, and then stored in a computer memory of any acceptable type.

In the context of this document, a computer usable or computer readable medium may be any medium that can contain, store, communicate, propagate, or transport the program for use by, or in connection with, the instruction execution system, platform, apparatus, or device, which can include any suitable computer (or computer system) including one or more programmable or dedicated processor/controller(s). The computer usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, radio frequency (RF) or other means.

Computer program code for carrying out operations of the example embodiments may be written by conventional means using any computer language, including but not limited to, an interpreted or event driven language such as BASIC, Lisp, VBA, or VBScript, or a GUI embodiment such as visual basic, a compiled programming language such as FORTRAN, COBOL, or Pascal, an object oriented, scripted or unscripted programming language such as Java, JavaScript, Perl, Smalltalk, C++, Object Pascal, or the like, artificial intelligence languages such as Prolog, a real-time embedded language such as Ada, or even more direct or simplified programming using ladder logic, an Assembler language, or directly programming using an appropriate machine language.

The computer program instructions may be stored or otherwise loaded in a computer-readable memory that can direct a computing device or system (such as described by example system 1 of FIG. 1), or other programmable data processing apparatus, to function in a particular manner, such that the instructions stored in the computer readable memory produce an article of manufacture including instruction means which implement the functions/acts specified herein.

The software comprises specialized computer program instructions that are executed by being provided to an executing device or component, which can include a processor of a general purpose computer, a special purpose computer or controller, or other programmable data processing apparatus or component, customized ad described herein such that the instructions of the specialized computer program, when executed, create means for implementing the functions/acts specified herein. Hence, the computer program instructions of the customized software are used to cause a series of operations to be performed on the executing device or component, or other programmable apparatus to produce a computer implemented process such that the instructions which execute on the computer or other programmable apparatus the steps for implementing the functions/acts specified in this disclosure. These steps or acts may be combined with operator or human implemented steps or acts and steps or acts provided by other components or apparatuses in order to carry out any number of example embodiments of the invention. The customized software may also utilized various commercially available software such as computer operating systems, database platforms (e.g. MySQL), or other COTS software, as desired.

For an example system, called the "Surgical Navigation Advanced Platform" (SNAP), medical images of an actual patient are transformed into a dynamic, interactive 3D scene. This dynamic and interactive image/model creates a new novel and original standard for medical imagery and has many applications.

The SNAP provides surgeons (neurosurgeons etc.), doctors, and their aids a unique virtual-reality guidance to determine the safest and most efficient pathway to remove tumors (cerebral etc.) and treat anomalies as vascular anomalies for example. The "Surgical Navigation Advanced Platform" (SNAP) can be used as a stand-alone system or an application of surgery navigation systems or used with a 3rd party navigation system for the type of procedures for which the 3rd party navigation system is used. These Procedures include but are not limited to Cerebral, Spine, and Ear, Nose Throat (ENT).

The SNAP allows surgeons to analyze and plan a specific patient's case before surgery, and then take that plan into the operating room (OR) and use it in conjunction with the navigation system during surgery. The SNAP then presents the navigation data into the advanced inter-active, high quality 3D image, with multiple points of view.

The SNAP is actually image guided surgery systems including a medical imaging device that present real time and dynamic multiple line of sights views (from different/ multiple perspectives) of the surgery procedure. The image includes the scanned medical image (based on scan such as CT, MRI, Ultrasound, X-ray etc.) and the surgery instruments. It may also include real time video and models based on video form microscope or other sources. The SNAP provides a real time 3D interactive guided image for the surgeon. The orientation of the anatomical structures (i.e. head, brain, knee, shoulder etc.) may be marked and pre-registered both in the physical/patient's and the scanned medical image (CT, MRI, Ultrasound, X-ray etc.); therefore, the orientation of the scanned medical image and the real anatomical structures of the patient's under the surgery are synchronized and aligned.

Furthermore, the above pre-registered markers provides a spherical reference for tracking the surgery instruments and the OR microscope (and/or the surgeon head) and therefore allowing to present the surgery instruments image/model in space in relation to the scanned medical image.

The patient's anatomical structures in 2D or 3D and the position and orientation of the surgery instruments may be synchronized in real time and presented to the surgeon with a real time location and orientation of the instruments and markers in space in relation to the anatomical structures.

The SNAP system is capable of preparing cases that have multiple scanned datasets. The built-in "Fusion" mode allows the user to select one dataset to serve as the primary dataset, and add secondary scan datasets, that will be aligned ("Fused") to the primary scan dataset.

The SNAP system has a unique clip features. The ANY plane IG cube clipping is a feature that the user can "clip" the 3D model from any desired angle, essentially cutting into the model and removing a section to expose the internals of the model. The clipping plane is the plane by which the 3D model is "Clipped" the plane defined by 2 variables—Plane normal (vector) and plane position (The point in space that the plane goes through).

Furthermore, the SNAP system knows to slave the ANY plane IG cube clipping to 3D moving elements in the scene. Since the cube-clipping plane is defined by a normal and a position, we can use moving elements in the scene to define this for the user. The elements are: The navigation probe, the 3D controller (Omni), the corridor, the IG point of view (Eye camera) etc.

Another feature is the Transfer Function. The SNAP system has a special ability to display "Tissue specific intensity". The original dataset slices are collected and stacked to reconstruct a cube of pixels, or what we call the voxels cube. The 3D model is a cube volume of voxels. The transfer function is used to map each voxel intensity value to color and opacity. That way we control the tissue intensity and enabling a surgeon to see what he typically can't see. This innovative feature allows surgeons to see behind arteries and other critical structures, something not possible until now.

The SNAP can present models on one or multiply windows on the same screen or on multiply screens. Examples for the features and applications of the SNAP, multiple features can be activated side by side on the screen.

Figure 2:
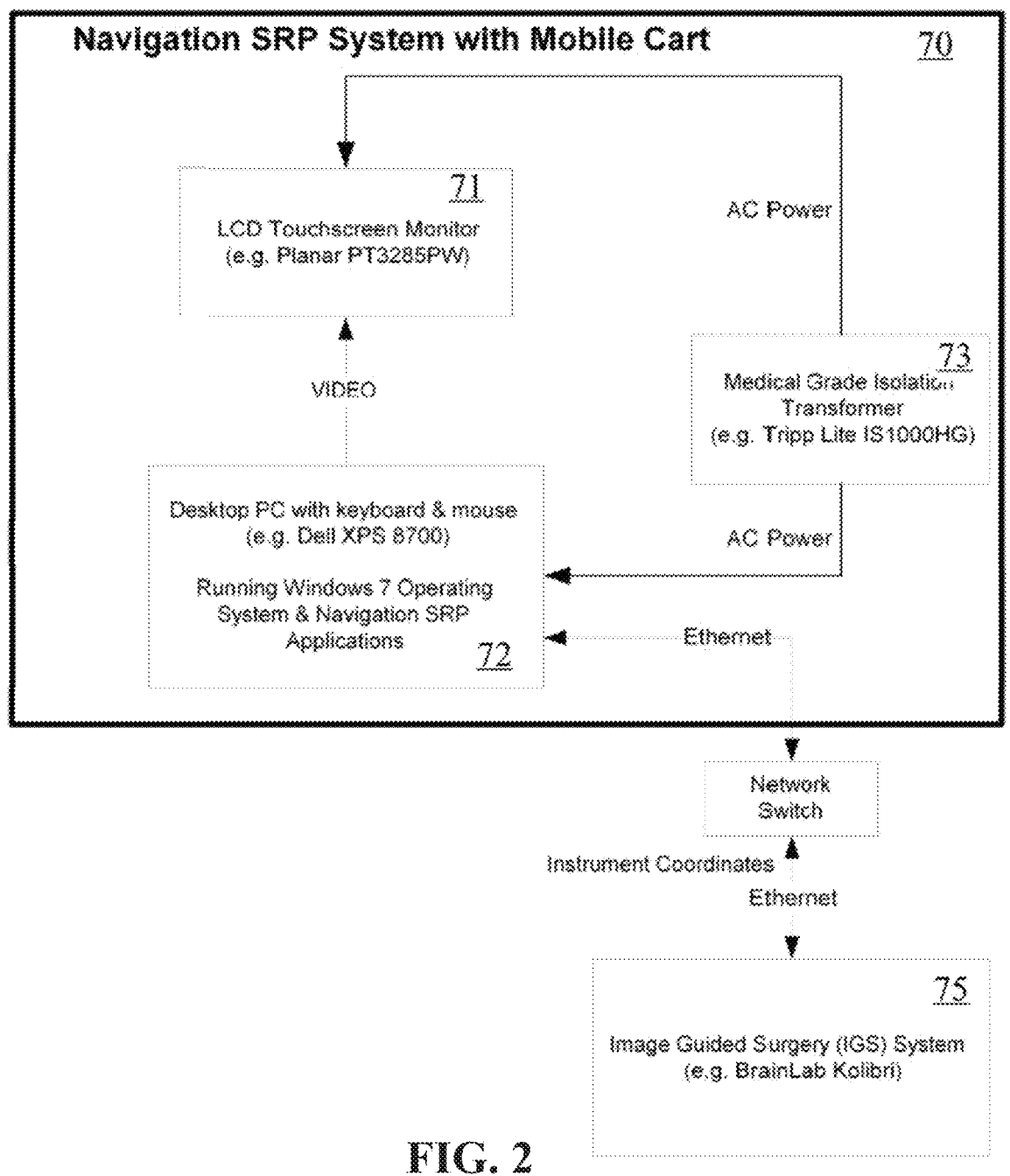
FIG. 2 illustrates a block diagram showing example SNAP tool components for the example SNAP system.

A typical SNAP system configuration is comprised of the following main components: (1) System mounted cart for mobility; (2) Medical grade isolation transformer; (3) a Personal Computer (or server) running Microsoft Windows 7 operating system; (4) a high end nVIDIA graphics adapter for high quality graphics; (5) a 27" or 32" full HD touch screen display; (6) a medical grade keyboard and mouse; and (7) a SNAP Software Application for implementing the features described herein. Such a system is shown by the block diagram of FIG. 2, where an example mobile cart mounted SNAP system 70 comprising a touchscreen monitor 71 is configured with a PC 72 and a power system 73, all of which can be provided in the operating room. The example system 70 is connected to a navigation system 75 provided in the operating room, such as the example Image Guided Surgery (IGS) System, from which the SNAP system 70 can receive data so that the SNAP system 70 can display high resolution, realistic 3D images that follow the operation of the navigation system, effectively enhancing the operation and display capabilities of the navigation system with the SNAP high-resolution imaging capability based on the images of the specific patient being operated on.

The Surgical Navigation Advanced Platform (SNAP) is intended for use as a software interface and image segmentation system for the transfer of imaging information from CT or MR medical scanner to an output file. A tissue segmentation window is provided to edit and update tissues segmentation to prepare a case. The change in tissue segmentation is reflected in the 3D image, and the result can be saved as part of the case file. It is also intended as both pre and intra-operative software for simulating/evaluating surgical treatment options. The Surgical Navigation Advanced Platform (SNAP) is a pre and intra-operative tool to simulate/evaluate surgical treatment options.

The system will typically provide EMC immunity that can be adapted for an operating room, and will utilize touch-screen operation for navigation, typing, and image manipulation. The system can store individual patient cases using a case file, which can be loaded into the system as desired. A surgeon can create a case from scratch, using scanned information (e.g., MR, or CT DIACOM image data files) and patient data of a particular patient. These cases can be edited and updated as desired. Editing windows can be used to edit and manipulate the images and files.

Generic models of various organs and tissues can be provided, which can be overlaid with patient specific models based on patient imaging or other diagnostic tools or laboratory inputs. Hence, for organs or other features not of particular interest, the system can use generic models (e.g., eyes or other organs) where patient specific information is not needed for the intended treatment.

The Surgery Navigation Advanced Platform (SNAP) displays patient specific dynamic and interactive 3D models with real time navigation data. When performing a navigation session, the tool can be used to verify the accuracy of the SNAP navigation pointer location (provided on the SNAP high resolution display) by pointing and touching visible structures on the patient (i.e. tip of nose, ear lobes)

and verifying that the pointer on the SNAP screen points to the same location in the 3D model.

Figure 3:
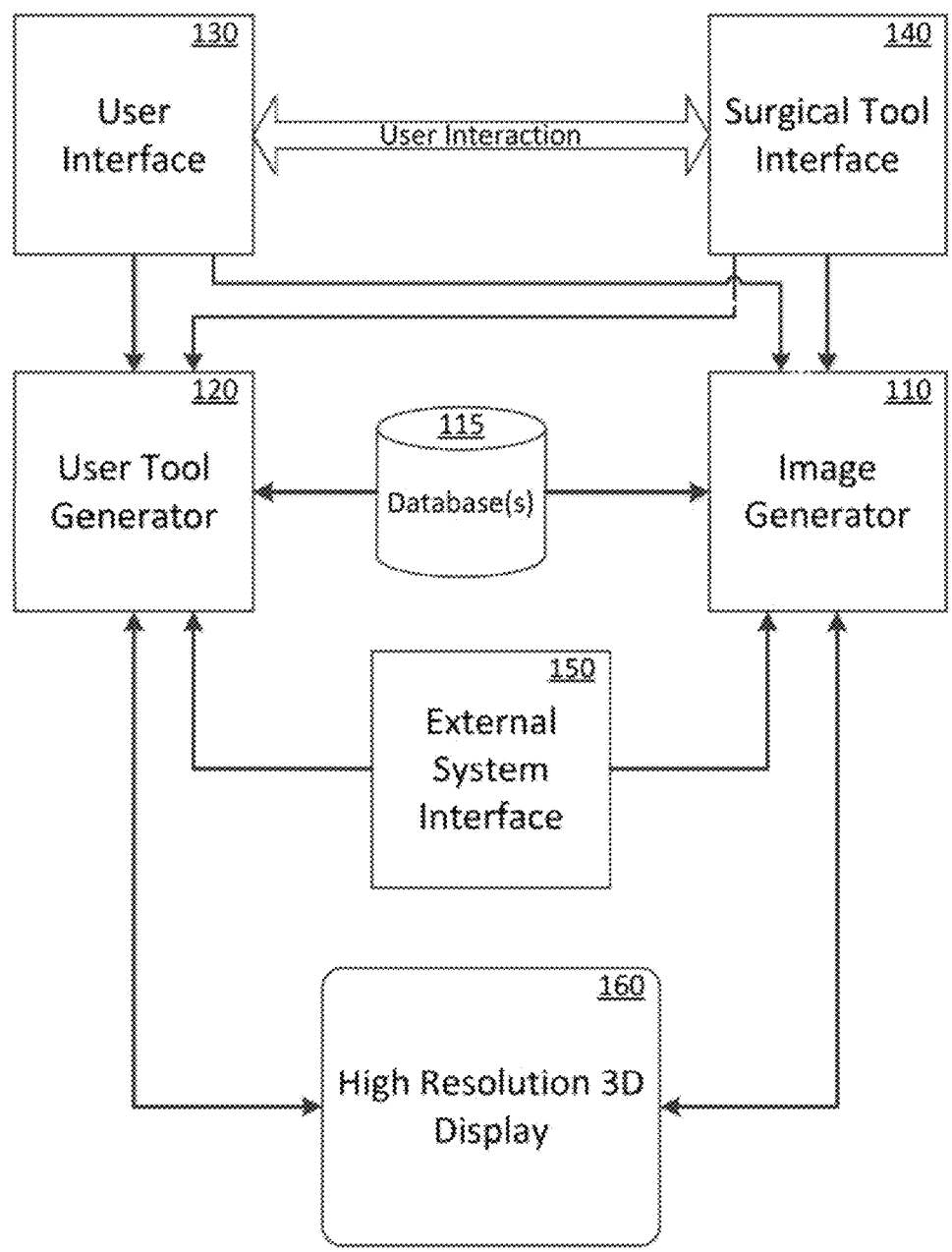
FIG. 3 illustrates a block diagram showing example software interfaces for the example SNAP system

FIG. 3 shows an example of the primary processing routines, driven by software modules, which generate the images provided by the SNAP tool. The Image Generator 110 generates the realistic tissue images for display on the display 160, using information stored on the database 115, such as generic tissue images, patient specific images, and the like. The image generator 110 assigns visual representation of each segment (shadow texture and so on) and the mechanical Properties and other modeling features will provide the realistic images.

Similarly, the user tool generator will generate realistic images of surgical tools that are displayed dynamically interacting with the tissue images generated by the image generator. In a surgical environment, the tool images displayed on the display 160 may represent actual surgical tool interfaces 140, representations of which could be generated for display by the image generator 110 or the user tool generator 120, for example. The surgical tool interface may dynamically interact with the tissue images generated by the image generator 110. Again, specifications and details about the tool images may be stored in the database 115. Note that because the display 160 may be a touchscreen display, the display 160 may act as the user interface 130, along with other devices such as a keyboard, mouse, or other input device. Also, the display 160 may include a Head Mounted Display as part of the display 160 to provide the surgeon and/or other participants a realistic visual image.

The SNAP tool also provides an external system interface 150 that allows the system to interface to other external systems that provide navigation or other functions to the surgeon, so that the SNAP tool can generate images that are consistent with the outputs of the external systems, e.g., mirror the navigation or update the imaging based on the operation of the external system(s). The SNAP tool can then update its display images appropriately for providing an integrated view to the surgeon in high resolution, 3D images that interact with the graphical tools.

Once the surgery tools and the other objects are selected by the surgeon, they are integrated into the virtual surgery scene displayed by the display 160 and turn into an integrated element of the simulated scenario including realistic visual features and mechanical properties and operation properties features that are applied to each one of those selected items, for example—displayed scissors have the real mechanical characteristics and will cut as the real scissors do, and, Aneurysm clips, when placed at the vessel, blocks the blood flow. In this manner, the displayed tools interact with the tissue models in a realistic manner, but in a way that surgeons can manipulate to provide viewpoints not possible in the real world, such as by making various features transparent, rotating images, reversing a procedure, etc.

The interactive image/scene that is displayed to the surgeon is constructed from elements that are both volumetric rendered elements and surface rendered elements. Furthermore, each element, volume or surface, interacts with one or more elements that are volume. Interaction between elements includes, but is not limited to, physical interaction such as: a collision model implemented to represent the interaction between elements that results with movements and/or reshape of elements that replicate the actual physical movements of the element according to physical conditions, such as pressure, elements material (elasticity, stickiness etc.), and collision condition such as collision angels and elements orientation.

The rendering process equation can account for all lighting shadow and shadowing phenomena and produce a final output stream that incorporates all the visual elements.

Anatomical structures that were created using a Tissue Paint or a Magic Tissue Wand algorithm and integrated with the scanned images are an integrated part of the image. For example, a vessel that anatomical structures that originally was partial and complete, after applying the Magic Tissue Paint and Tissue Wand algorithm will become a complete anatomical structures with structure that is combined from the original scanned image and the new created structure. Furthermore, a control (check box) allows to select the new created structure and to switch between on (showing the new created structure) or off (hiding the new created structure). Additionally, an option is provided for selection to render the new created structure in a volume and or mash/polygon rendering/reconstruction.

A developed algorithm and software tool provides the user an interface to draw any geometric shape or free hand drawing shape in 2- or 3-dimensions (e.g., line, circle, clinic, ball etc.). The region that is included/enclosed/captured within the said geometric shape (2- or 3-dimensions) is defined as a "Marked Region". The user then, has the ability to define and assign any visual characteristics and any mechanical properties to that "marked region" including the ability to paint portions of images, make them transparent or shade them, for example. Virtual light sources can be provided with characteristics that include: spherical location in space, color of the light, strength of the light, the aspect ratio, the geometric shape of the virtual source etc.

Structures that are created with the Tissue Paint, Magic Tissue Wand algorithm or the Marked Region can be assigned with desired mechanical properties characteristics. The mechanical properties coefficients of any anatomical structure (stiffness, elasticity etc.) can be tuned by the user to create a tailored made mechanical behavior.

The system provides Real Time Tracking and Feedback to track a real surgery instrument during the surgery. The tracking system transfers the surgery instruments location and coordination in space relative to the orientation and location of a real anatomical structure (for example, specific spot on the patient's head). The instruments' location and orientation is then sent to the surgical simulating system. Feedback is provided to the surgeon based on the patient specific simulation and the instruments' location and orientation. One example for such feedback can be; the system generates feedback to the surgeons for the type of tissue he is dissecting and alarming the surgeon in case that he dissects healthy brain tissue instead of a tumor. Additional example is that after that the surgeon applied an implement on the real anatomical structure (for example an aneurysm clip applied on an aneurysm on the real patient), the system allows the surgeon to rotate the simulated image/model that is princely oriented as the real anatomical structure based on the tracking, and observe and evaluate the location and efficacy of the placed implant.

This tracking and feedback of the real instrument can be accomplished in a number of ways, such as by using a video system to track the location and movement of the instrument and the patient features. Alternatively (or in addition to video tracking) the surgical instrument may be modified to enable tracking, such as by using GPS, accelerometers, magnetic detection, or other location and motion detecting devices and methods. Such modified instruments may communicate with the SNAP tool using WiFi, Bluetooth, MICS, wired USB, RF communication, or other communications methods, for example (e.g., via surgical tool interface 140 in FIG. 3).

The SNAP system is enhanced and modified for using the MD6DM features to incorporate the augmented reality surgical system described herein below. The MD6DM provides a graphical simulation environment which enables the physician to experience, plan, perform, and navigate the surgical intervention in full spherical virtual reality environment, with the addition of augmented reality features greatly expanding the functionality and usefulness of the SNAP system described above.

Figure 4:
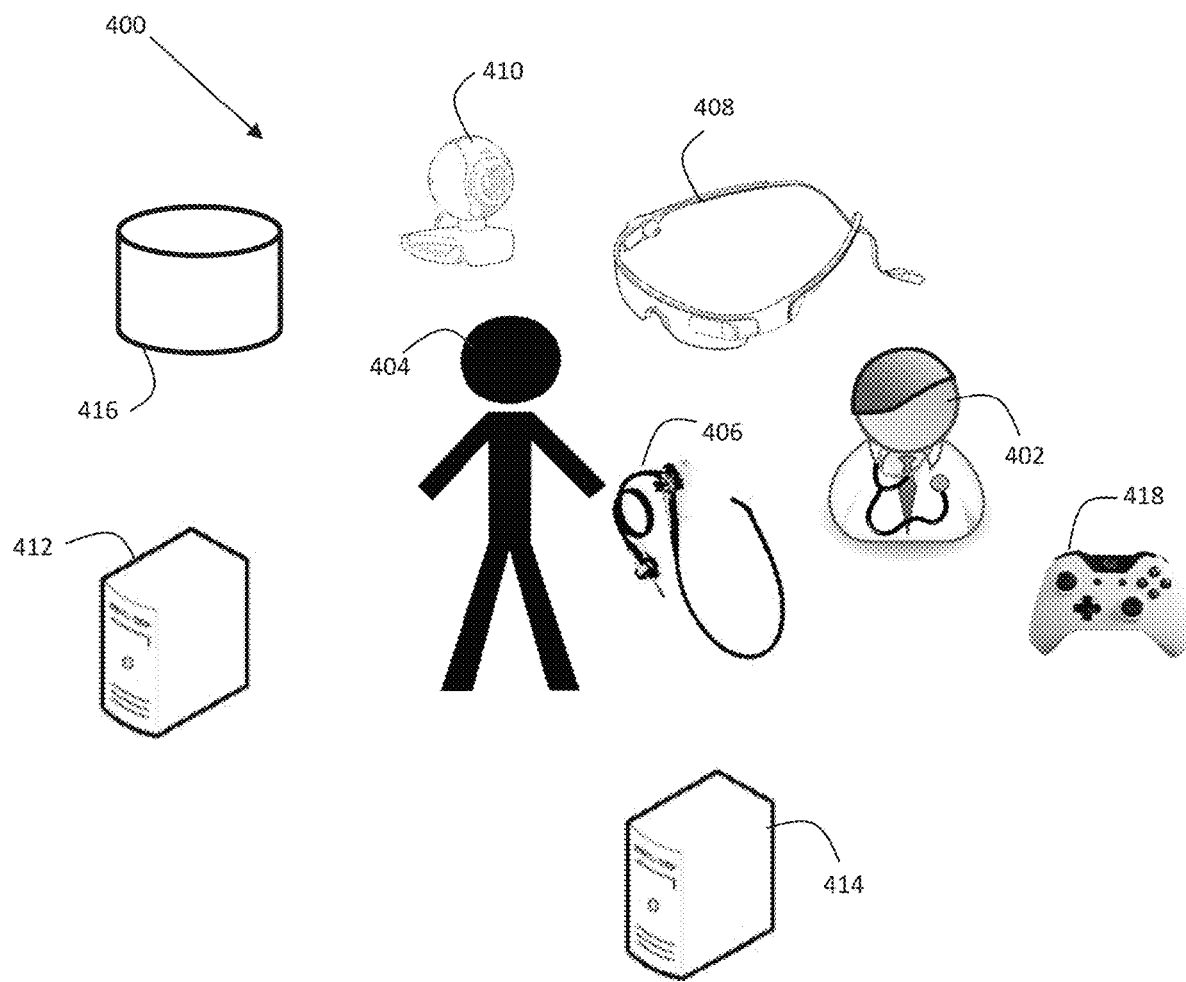
FIG. 4 illustrates an example Augmented Reality Surgical System.

This modification results in a Dual Mode Augmented Reality Surgical System ("ARS") 400 described herein and illustrated in FIG. 4, which gives the surgeon 402 or another user (such as assistants, nurses, or other doctors) an integrated view of a data content injected from an external source along with the optic view of the patient 404 on the same head-mounted display ("HMD") 408. This integrated view, provides the surgeon 402 with a "Superman" type of view of the patient 402. In other words, by wearing the HMD 408, and connecting to a 360 MD6DM model for example, the surgeon 402 is able to look at the patient 404 and "see inside" the body. This is because the 360 model, which is based on CT and MRI images of the patient 404 is aligned with and projected onto the patient via the HMD 408 view. Thus, when the surgeon 402 looks at the patient 404, it's as if he can see internal structures of the patient 404 such as a tumor or blood vessels, as if the patient's 404 body was transparent. The surgeon 402 can then walk around the patient 404, as will be described further, and the transparent views are auto aligned with the new perspective/angle according to the surgeon's 402 perspective relative to the patient 404. The surgeon 402 can thus perform procedures on the patient 404 while having "Superman" or "x-ray" information about the patient 404 and knowing exactly what structures or obstacles will be faced during the procedure. For example, if a surgeon 402 drills into a skull, he may use the HMD 408 to anticipate and identify what lies underneath the skull at the trajectory point of the drill and to adjust the procedure and drill path accordingly as needed in order to reach the desired area efficiently for treatment. It should be appreciated that other procedures, such as for example procedures involving the heart, liver, etc. may also benefit from using the HMD 408, even though examples herein may refer to the brain specifically.

It should be appreciated that the data content may include various types of data being injected from various data sources and received at the ARS computing system 412 for integration with the optic view of the patient 404. For example, the data feed may include a live video feed from an endoscope 406 (or any type of video camera 410), a SNAP model received from a SNAP system 70 described in FIG. 2, data such as medical records specific for that patient 404 injected from a medical records data system 414, or any other suitable data content that a surgeon 402 may find beneficial to view during a surgical procedure without looking away from the patient 404.

It should be appreciated that the HMD 408 is see-through or transparent. Thus, the surgeon 402 may still have a visual of his own hands or tools while engaging with the patient 404 and simultaneously seeing the injected content such as the 360 model. In one example, the HMD 408 may be a mixed or marriage reality display wherein an external camera captures live real time video of the surgeon's 402 hands or tools being used and injects and auto-merges the live video feed into the augmented reality view via the HMD 408. Thus, the surgeon 402 is able to maintain a view of his own actions via his hands or tools while simultaneously having the "Superman" view of the inside of a patient, along with any additional augmented content as appropriate. It should be appreciated the reference to a tool may include a free-hand tool operated by the surgeon 402 or any kind of robotics tool operated by a computer or robot either autonomously or via human control.

It should be appreciated that although the ARS computing system 412 is described as a distinct computer system from the SNAP system 70, in one example, the SNAP system 70 may be incorporated with the functionality of the ARS computing system 412 described herein to provide a single streamlined ARS computing system 412.

As will be described in more detail, the ARS computing system 412 may operate in one of two modes selected by the surgeon 402. In particular, the ARS computing system 412 may operate in one of a tracking or non-tracking mode. In a non-tracking mode, the ARS computing system 412 injects content into the HMD 408 without regard for the position or location of the HMD 408 or the surgeon 402. In other words, the injected content may remain static as viewed via the HMD 408, even as the surgeon moves his head and views the patient 404 from different angles and perspectives. In a tracking mode, the HMD 408 includes a mechanism for tracking location and position relative to the patient 404. Therefore, the ARS computing system 412 may inject content into the HMD 408 based on the tracked position of the HMD 408, and therefore the position of the surgeon 402. For example, the surgeon 402 can inspect specific patient 404 anatomy both in the pre-built model as well as live in the patient 404 simultaneously. The system 400 gives the ability to step into the MD6DM model and physically move the user's body and look around at specific structures. The user can look 360° around a targeted anatomy or pathology, and explore behind pathology to see how it is altering the patient anatomy.

It should be appreciated that, although a tracking mechanism is described as being incorporated into the HMD 408, the tracking mechanism may be a separate device (not shown) positioned on the surgeon 402, at or proximate to the HMD 408. In one example, tracking is accomplished using a camera integrated into or near the HMD 408. The camera is configured to recognize relative markers on the patient 404 and to determine a surgeon's 402 position as well as angle and direction of view relative to the patient.

It should be appreciated that leveraging such internal tracking techniques, as opposed to external tracking techniques enables a lightweight and flexible solution that can be used in an emergency room or an intensive care unit for example, where space and resources may be more limited than in an operating room where external tracking mechanisms may be available.

It should be appreciated that with the ARS system 400, the surgeon 402 no longer needs to take his eyes off the patient 404 in order to look at a feed from microscope or endoscope 406, patient scans, planning software or a MD6DM model because the data content and the real optical image are overlaid on the Head-Mounted Display (HMD) 408.

It should be further appreciated that all or part of the SNAP system 70 as described above and shown in FIG. 2 modified to incorporate the features of MD6DM, enables the ARS system 400 by obtaining patient DICOM 2D images and building virtual models in real time or obtaining prebuilt models. Data is obtained from a database 416, for example. The ARS Computing System 412 leverages the virtual models, as well as other data inputs, including tracking data if operating in a tracking mode, to form an augmented reality view of the patient 104.

The ARS system 400 further includes a control means, such as controller 418 for example, for interacting with and manipulating the different injected data content. It should be appreciated that various suitable types of control means may be used in place of controller 418. In one example, foot pedal or interface maybe used to interact with and manipulate the injected data content. In one example, voice recognition technology may be incorporated into the HMD 408 in order to receive, interpret, and process control commands from the surgeon 402. Control commands for interacting with and manipulating data content may include, for example, instructions to cycle through the different data content sources during a surgical procedure. For example, the field of view via the HMD 408 may be limited and therefore the ARS computing system 412 is configured to display a limited number of windows or views corresponding to a limited number of data sources. However, a surgeon 402 may wish to view, interact with, and manipulate data content from more than one source during a surgical procedure. Accordingly, the controller 418 may enable the surgeon 402 to select data corresponding to different data sources to be displayed at appropriate times as needed. It should be appreciated that control means including a foot pedal or voice recognition technology enables the surgeon 402 to perform such interactions even when the surgeon's 402 hands are occupied during a surgical procedure without distraction and with minimal pause.

In one example, control means for interacting with and manipulating data content may leverage the motion tracking capabilities of the ARS system 400. For example, a surgeon 402 may desire to view a first data content received from a first data source while viewing the patient 404 at a first position but then may desire to view a second data content received from a second data source while viewing the patient 404 at a second position. Accordingly, the ARS computing system 412 may be configured to inject the first data content while the surgeon 402 is in a first position but then switch to the second data content while the surgeon is in a second position. In one example, data content may appear or disappear depending on the angle of view of the surgeon 402. For example, the surgeon 402 may not desire to view a patient's 404 medical record directly in line with viewing the patient 404 but may desire to see the medical record by briefly glancing over to a specific direction.

It should be appreciated that, in addition to selecting the source of content being injected for display, the surgeon 402 may also use the controller 418, or other control means described, to interact with and navigate the selected data content. For example, the controller 418 may be used to scroll or navigate through a patient's 404 medical record, to navigate a SNAP model, and so on.

It should be appreciated that, in one example, the various types of content described herein that may be injected into the HMD 408 and integrated to form an augmented reality view may also similarly be fed into a monitor or display screen in order for the information and content to be viewed by many people inside a room or setting via a single display.

Figure 5A:
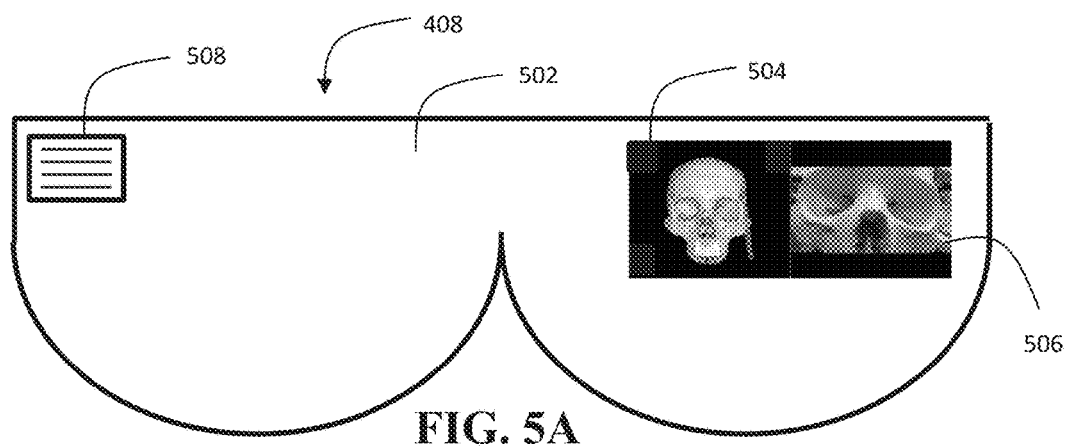
FIG. 5A-5C illustrates example augmented reality views via the HMD.
Figure 5B:
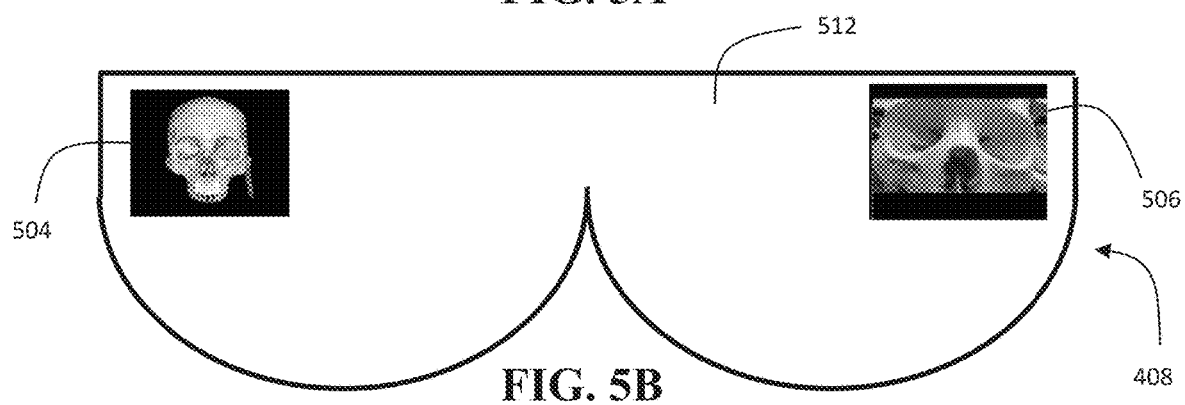
Figure 5C:
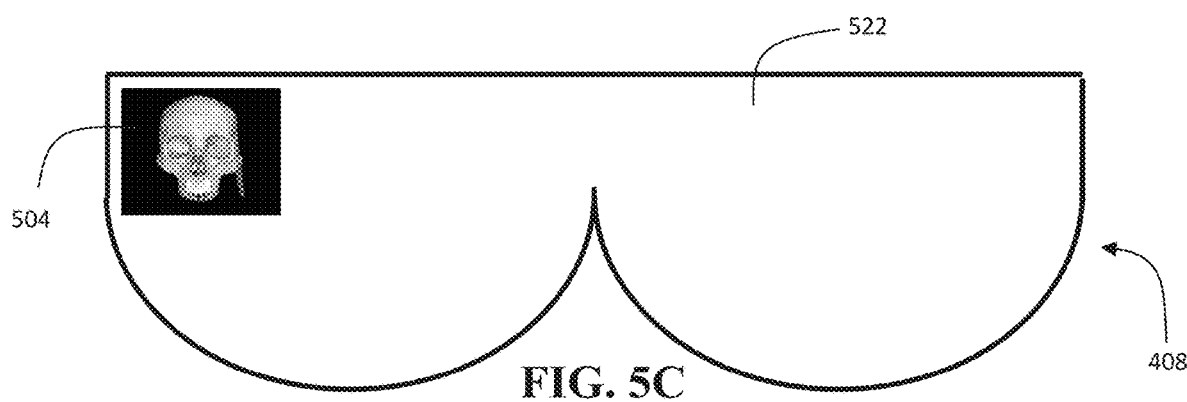

It should be appreciated that the multiple types of views may be generated by the ARS computing system 412 for viewing via the HMD 408. For example, as illustrated in FIG. 5A, am augmented view 502 via the HMD 408 may include a 3D model 504, a live video feed 506, and a patient record 508. It should be appreciated that, although the example augmented view 502 illustrates data content injected from 3 different data sources, data content from any suitable number of data sources may be injected into the augmented view 502. It should be further appreciated that, although in the example illustrated the injected data content is arranged in a specific manner, including the 3D model 504 adjacent to the live video feed 506 positioned in the top right of the view 502 and the patient record 508 in the top left of the view 502, the different data content may be arranged in any suitable manner. For example, as illustrated in FIG. 5B, augmented view 512 includes data content injected from 2 different data sources, positioned in at opposite ends within the augmented view 512. FIG. 5C illustrates a further example in which augmented view 524 includes data content injected from a single data source.

Figure 6:
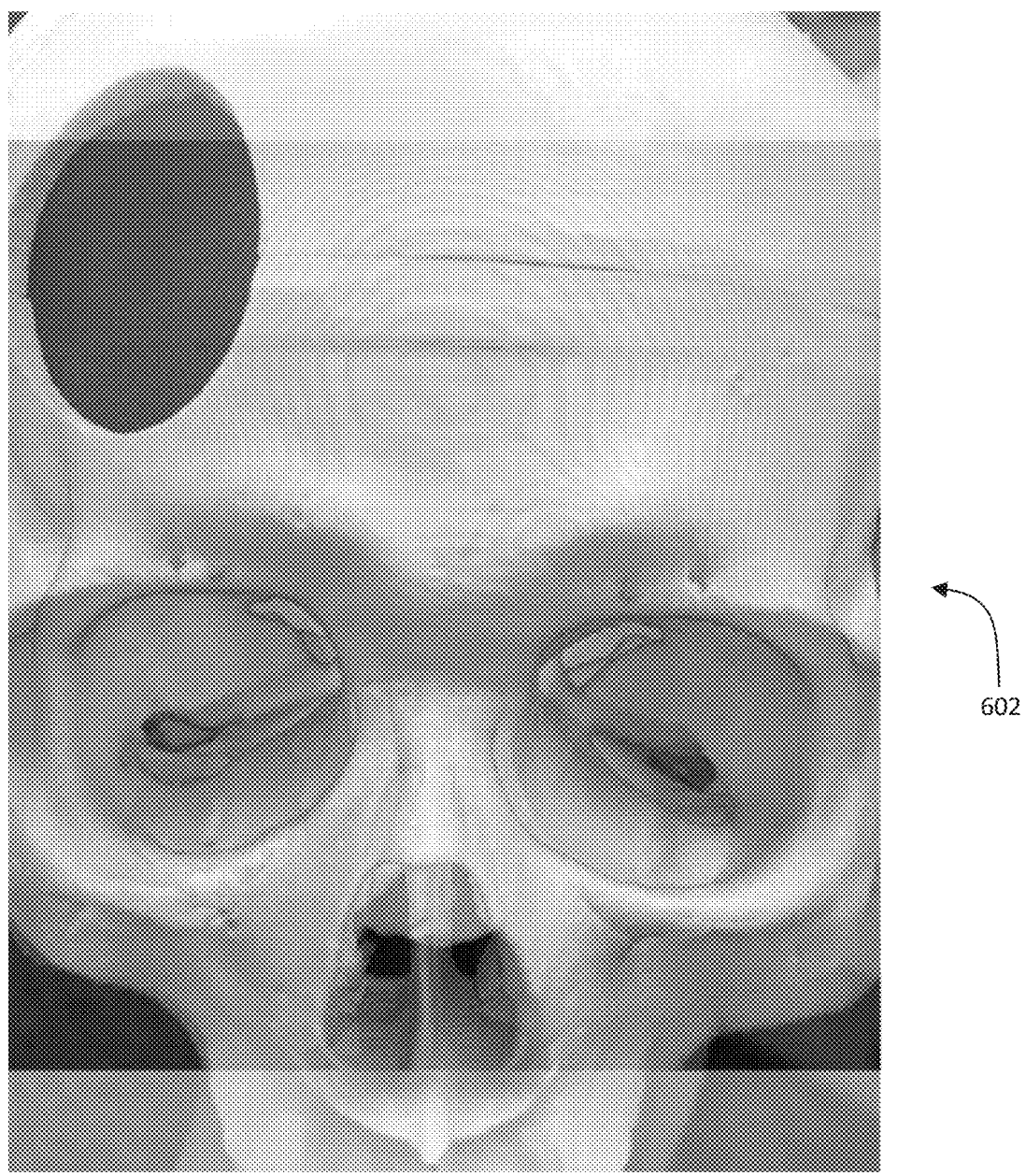
FIG. 6 illustrates example augmented reality view.

FIG. 6 illustrates an augmented view 602 including a 3D model on top of an optical view of the patient. It should be appreciated that in order for the 3D model to accurately line up with the optical view of the patient, the ARS computing system 412 should be operating in a tracking mode. It should be further appreciated that any combination of augmented views may be presented via the HMD 408, including injecting data that does not require tracking, such as a patient record, with data that may benefit from tracking, such as the 3D model. For example, an example augmented view (not shown) may present a 3D model on top of an optical view of a patient in tracking mode as well a patient record, which may not require tracking, off to one side.

The layout of an augmented view, the sources of data content, as well as the number of sources of data content that the ARS computing system 412 injects into the augmented view may be predefined by a systems administrator. In one example, the ARS computing system 412 may be configured to enable a surgeon 402 to adjust the positioning and layout of the augmented view in real-time via the controller means described.

Figure 7:
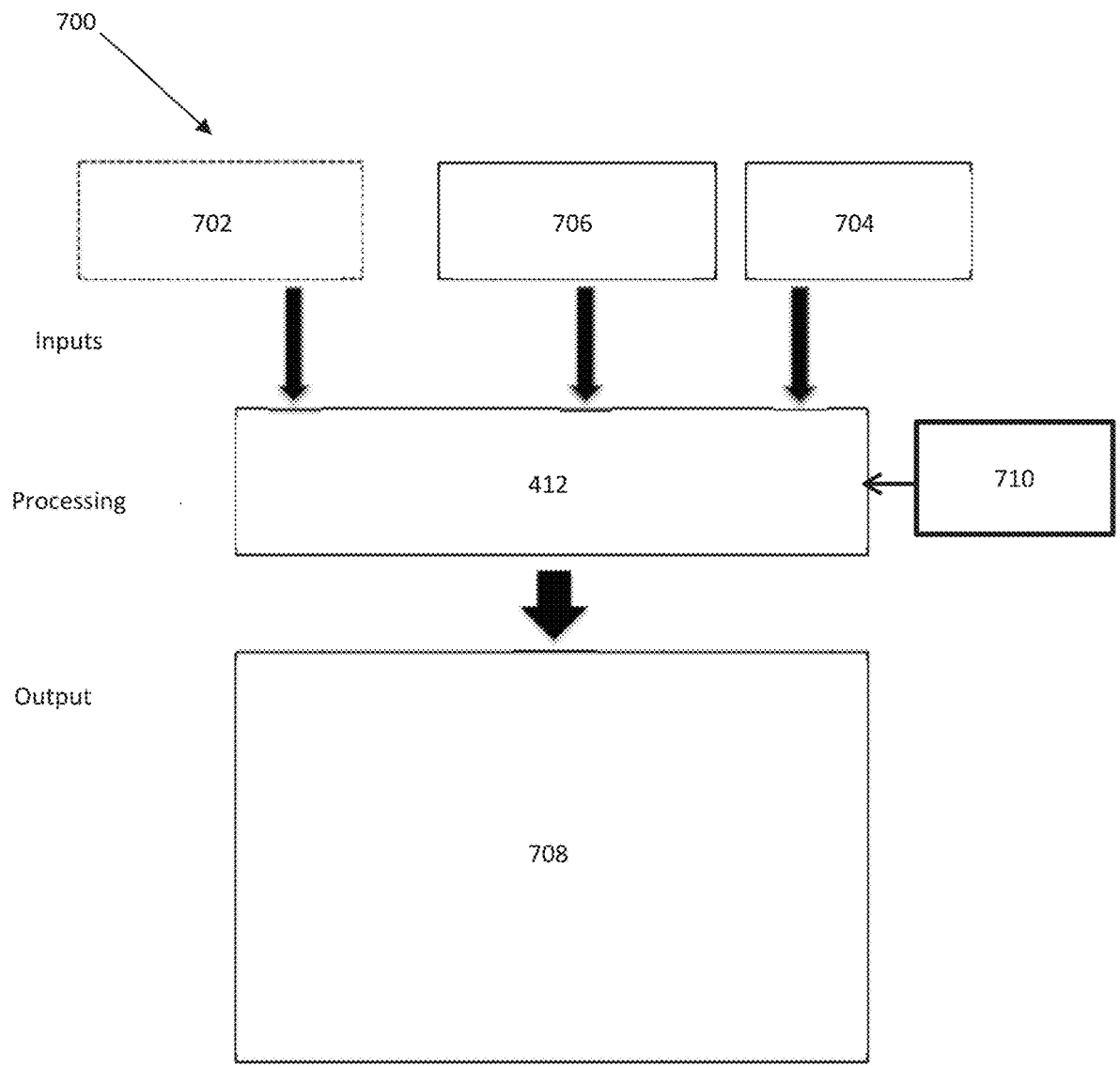
FIG. 7 illustrates a block diagram of an example Augmented Reality Surgical System.

FIG. 7 illustrates an example block diagram of the ARS system 700. The ARS computing system 412 is configured to receive, as a first input, a SNAP 3D model 702. The ARS computing system 412 is further configured to receive, as a second input, a live video feed 704. When operating in tracking mode, the ARS computing system 412 is further configured to receive, as a third input, navigation system tracking data 706. In one example, the tracking data 706 is indicative of the position and orientation of a surgeon 102 relative to the patient 104. It should be appreciated that, based on such navigation system tracking data 706, the ARS computing system 412 is able to determine not only where in a room a surgeon 102 is positioned but also where the surgeon 102 is looking. For example, a surgeon 102 may be positioned on the right side of a patient 104 body. However, the surgeon 102 may view, from that position, a top of the patient's 104 head or a side of a patient's 104 head, for example. It should be appreciated that the ARS computing system 412 is able to calculate and pinpoint the angle of view in addition to location and therefore offer a more unique and distinct experience for the surgeon in the operating room. The ARS computing system 412 is further configured to receive guidance or control input 710 from a control means, such as the controller 418.

The ARS computing system 412 processes the inputs 702 and 704, based on the tracking input 706 and guidance/control input 710, and injects them into the HMD 408 to form an augmented reality view of the patient 404. It should be appreciated that the ARS computing system 412 may be configured to receive any suitable number of inputs from a variety of suitable input sources in order to provide the surgeon 402 more complete information that may be helpful for performing a particular surgery. For example, the ARS computing system 412 may be configured to receive, patient medical records, additional live video feeds, or additional tracking and sensor information indicative of a surgeon's location within the operating room.

In an example in which the ARS computing system 412 operates in a tracking mode, the ARS computing system 412 is configured to present the SNAP 3D virtual model to the surgeon 402 via the HMD 408 such that the virtual model overlays the surgeon's 402 actual view of the patient 404 in order to provide the surgeon with an augmented reality view of the patient 404. The ARS computing system 412 relies on the navigation system tracking data 706 to synchronize the virtual model presented with the surgeon's 402 actual view of the patient 404. However, even when operating in a non-tracking mode, the SNAP 3D virtual model may still be injected into the augmented view via the HMD 408 and presented to the surgeon 402, although it should be appreciated that without tracking capabilities enabled, the SNAP 3D virtual will not automatically align with and overlay the actual view of the patient 404 and will instead require some form of guidance or control input 710 to navigate.

It should be appreciated that, in a tracking mode, the augmented reality view may continuously be updated in real time as a surgeon's 402 position, orientation, or angle of view changes. Thus, as the surgeon 402 moves around the patient or adjusts his focus on a different position on the patient 404, the virtual model is adjusted so that the augmented reality view is synchronized with the such movements and stays true to the surgeon's 402 perspective.

Furthermore, the system can accommodate any number of additional users, such as additional surgeons, nurses, assistants, or others who may be present locally or located remotely and connected to the system via a communication network such as the Internet. The system can utilize information from any or all of these additional users to further augment the view using information from such additional users, such as the actions of a second surgeon supporting the medical procedure. In addition, the system can provided the augmented images as seen by the surgeon to any of these additional users, whether using an HMD display or some other type of display. Hence, is some embodiments, the action of assistants, such as nursed to assist the procedure could also be displayed as part of the augmented view, or as an additional augmented view.

Referring again to FIG. 4, it should be appreciated that the surgeon 402 can interact with the ARS system 400, and in particular with the different data content such as the SNAP 3D model, in several ways including, for example:

Head movements—In tracking mode, using a rotational sensor of the HMD 408, the ARS system 400 may track the surgeon's 402 head movements and angles. This allows the user to interact with data content based on their movement and angle adjustments.

Controller—Using the a controller 418, the surgeon 402 can move in the desired direction with arrow keys or using other buttons, is able to activate specific functions associated with the data content.

Voice—Speaking keywords or phrases that are received by a sensor such as a microphone activates a specific functionality. For example, "Jump to marker 1" will move the user to the predefined marker 1 position. When Collaboration is available, "Move to Player 2 view" moves the primary user to the 2nd "Player's" position, and orients the primary user's view to the 2nd "Player's" orientation at that time.

Position sensor—In tracking mode, using a position tracking sensor to track movements, the movements of the surgeon 402 will be translated to virtual movement or other associated functions within the data content.

In tracking mode, the surgeon 402 interacts with the SNAP 3D model in addition to seeing the real world. The SNAP 3D model is virtually positioned at a surgeon-designated place in the real world environment. It should be appreciated that positions may include, in addition to above the patient, over a table in the room, over a 3D printed part of the patient, in line with a tool with special markers, and any other suitable place in the room.

It should be appreciated that a registration process may be required to align the SNAP 3D model received from the database 416 to a patient's 404 anatomical part. Alignment is based on the information retrieved from the patient's own pre-operative scans (upon which the SNAP 3D model has been built), and alignment/registration process information. In one example, alignment is achieved by receiving the registration information from tracking means incorporated into the HMD 408 or an independent tracking device (not shown) on the surgeon 404 at or near the HMD 408 and aligning the case based on the received information. In another example, alignment is achieved by allowing the user to manually align it to the anatomical structure. This may done using the Controller 418, for example.

It should be appreciated that, although references throughout the description may be made to using the system 400 in connection with a surgical procedure for a brain tumor in particular, the system 400 may similarly be used on a variety of surgical applications on various anatomical parts of the patient 404.

In order to enable tracking mode while providing a lightweight solution that does not rely on external hardware in a hospital room, the HMD 408 includes an internal tracking mechanism, rather than relying on external tracking mechanisms. By incorporating both the SNAP 3D model as well as other appropriate data content into a single augmented view, the HMD 408 displays all the information the surgeon will need during the surgery. In particular, the surgeon can access live video from his point of view (via an Endoscope, microscope etc.), see the scans of the patient, and view medical records, for example, all without taking his eyes away from the patient 404.

In one example, the orientation of the anatomical structures (i.e. head, brain, knee, shoulder etc.) is marked and pre-registered both in the physical patient and the scanned medical image (CT, MRI, Ultrasound, X-ray etc.). Therefore, the orientation of the scanned medical image and the real anatomical structures of the patient being evaluated in surgery are synchronized and aligned. In one example, the HMD 408 may have a built-in HD optical system (microscope, camera etc.) that will be synchronized and aligned with all the scanned images and the SNAP 3D model. This allows for the elimination of the traditional surgical microscope, and the current limitations of those systems. Without changing glasses and loops, a larger number of surgeons can collaborate "under microscope" conditions using individual HMD's 408 and head docking stations above the real patient. Head docking stations serve to keep the very intricate scenes steady for direct operators in critical microsurgical environments, while allowing external viewers to appreciate the exact same AR-enhanced "under scope" scene.

Figure 8:
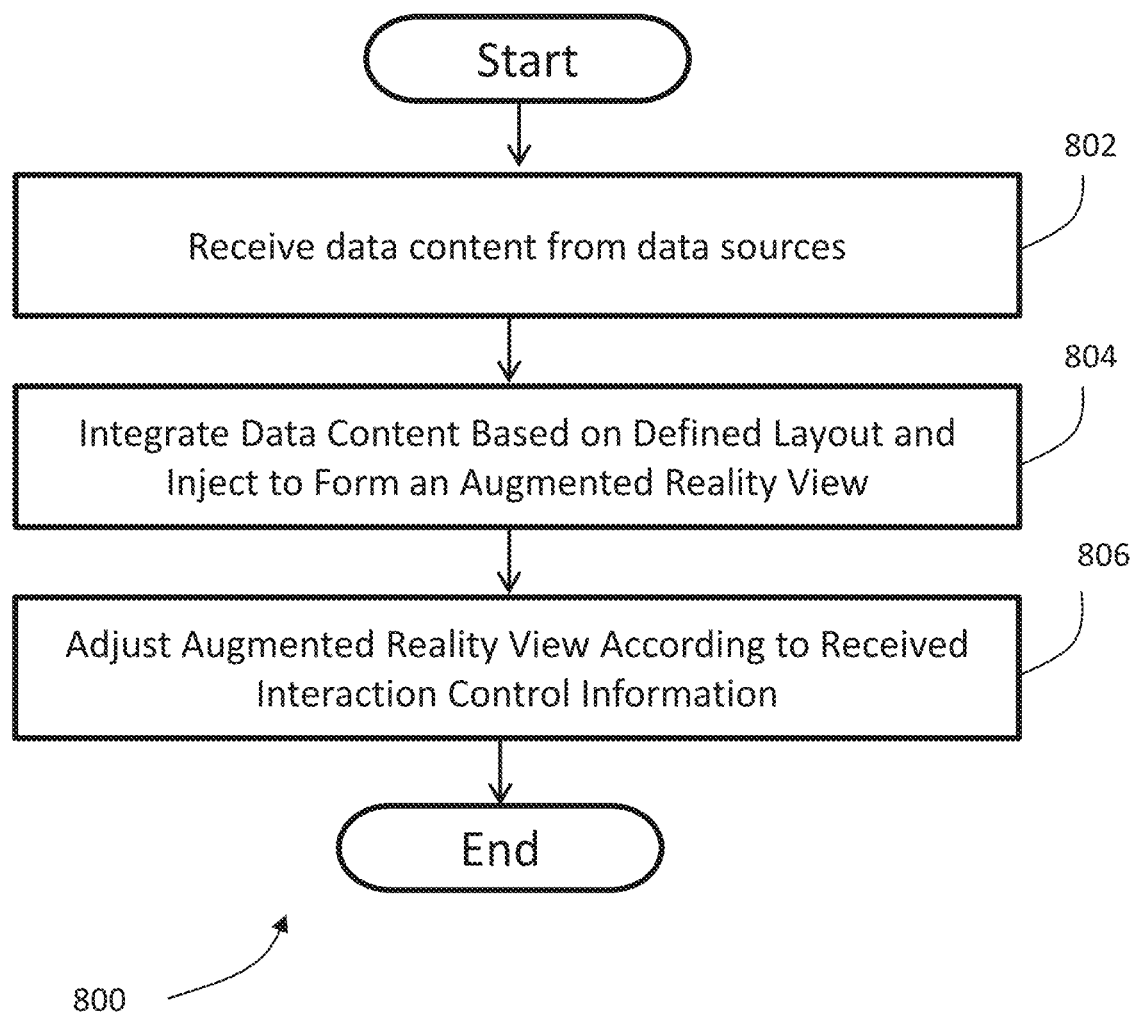
FIG. 8 illustrates an example Augmented reality surgical method.

The ARS system 400 will be further appreciated with reference to a method 800 of use illustrated in FIG. 8. At step 802, data content is received at the ARS computing system 412 from one or more sources. In one example, receiving data content may include patient specific DICOM (CT, MRI etc.) data being uploaded into the ARS computing system 412 and being processed to create the SNAP 3D model. Receiving data may also include receiving patient records, receiving a live video feed, and/or receiving control/guidance information. In one example, in tracking mode, the step of receiving data content may also include receiving tracking information from an internal tracking mechanism.

At step 804, the ARS computing system 412 integrates the different data content received from the data sources and injects the data content into the view of the HMD 408 in accordance with a defined layout to form an augmented reality view such as one illustrated in FIGS. 5A-5C and FIG. 6. In one example, in tracking mode, the step of integrating the data content may further include aligning a SNAP 3D model with the optic patient view based on received tracking information.

At step 806, the ARS computing system 412 uses received control/guidance information to adjust the injected data to alter the augmented reality view. For example, the ARS computing system 412 may cycle through different data content injected into the augmented reality view responsive to the surgeon 402 making such selections via a control means. In one example, the ARS computing system 412 may manipulate the data content responsive to input received from a control means. In one example, in tracking mode, the step of adjusting the injected data to alter the augmented reality view includes updating the SNAP 3D model alignment with the optic patient view based on updated tracking information received in response to the surgeon 402 moving and therefore causing updated tracking information to be communicated to the ARS computing system 412.

In example application, the ARS system 400 is configured to assist a surgeon 402 with performing a craniotomy. For example, craniotomy content data may be received that is indicative of a desired target on the skull where the procedure should be initiated. Using tracking data, the craniotomy content data may be injected into and aligned with an optical view of the patient 404 to form an augmented realty view which will guide the surgeon 402 during the procedure. It should be appreciated that the ARS system 400 may aid in significantly eliminating craniotomy errors by providing such an augmented reality view to the surgeon 402. In particular, such an augmented reality view may aid in improving procedure accuracy, which may typically be only 75%. In another example application, the ARS system 400 may similarly be used to assist a surgeon 402 with inserting a catheter more accurately into the patient 404.

It should be appreciated that there are many systems in the operating room which track the user status during surgery and which may provide a surgeon with relevant information that has not been discussed here. Accordingly, it should be appreciated that the ARS system 400 enables the HMD 408 to present to the surgeon 402 an augmented reality view which may include any suitable combination of such relevant information. This allows the surgeon 402 to remain focused on the surgery while still being able to process needed information during surgery, without taking his eyes off of the patient.

In one example, the ARS system 400 and method 800 described herein may be used in a collaboration mode. In this mode, the surgeon 402 can choose to allow other remote users to join in and either observe or assist with the procedure when desired. Users may communicate with remote users as follows: 1) Headphone/Speaker are used to hear all other remote users; 2) a Microphone is used to talk to all remote users; and 3) a video stream of remote users may be included as one of the data content being injected into the augmented reality view of the HMD 408.

Figure 9:
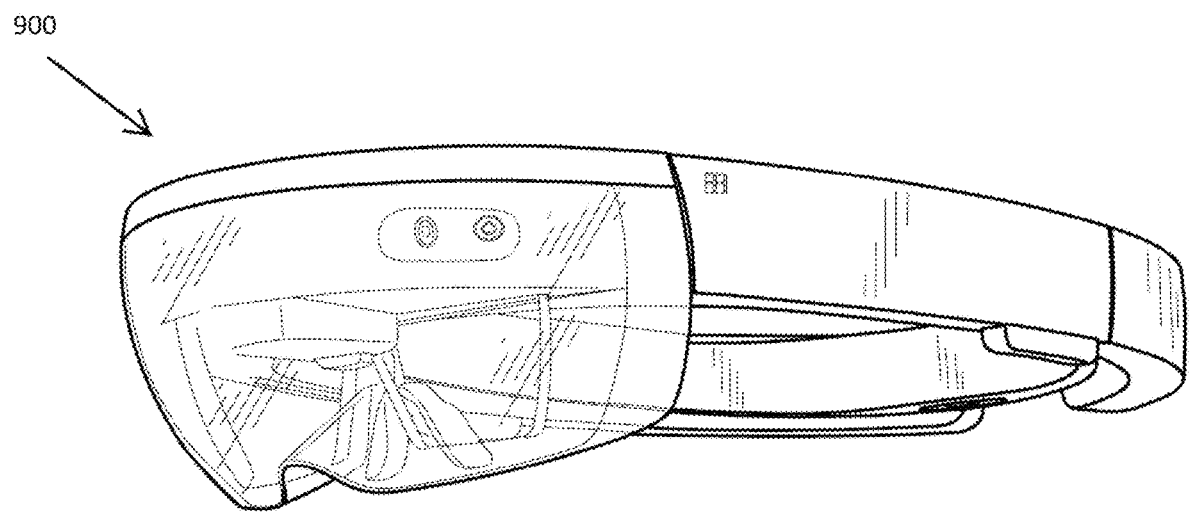
FIG. 9 illustrates an example head mounted display (HMD).

It should be appreciated that any suitable type of head mounted display (HMD) 408 may be used with the ARS system 400. FIG. 9 illustrates an example of a HMD 900. HMD 900 includes a wireless antenna (not shown), for example. Accordingly, the HMD 900 may operate wirelessly and therefore eliminate the need for extra cords in the operating room.

HMD 900 further includes a processor and memory (not shown). Thus, in one example, the HMD 900 may be configured to receive, store, and process data content without relying on the ARS computing system 412. For example, the HMD 900 may be preloaded with the appropriate data content relevant for a specific patient and procedure before entering a hospital room to perform a surgical procedure. This offers a lot more flexibility and mobility within the hospital room without the need to bring in extra equipment into an already crowded room.

In one example, a HMD 900 may not have sufficient memory or processing capabilities to store and process all data content. Thus, in one example, the ARS computing system 412 may be configured to generate light or stripped down versions the data content and transfer the light versions to a HMD 900 before the surgeon 402 takes the HMD 900 into the hospital room to perform a surgical procedure.

It should be appreciated that the example system and method described herein may be scaled in several ways. For example, although the example system and method may have been described with reference to a single HMD, it should be appreciated that the system may comprise multiple surgeons or users with multiple HMDs within an operating room during a surgery, all relatively simultaneously receiving their own custom augmented reality experience based on their location and orientation within the room. In addition, remote users not present in the OR at the time of the surgery, or even a user that is present in the OR, may experience an augmented reality experience from the perspective of one of the other users in the OR.

It should be appreciated that any number of suitable input sources may be integrated into the augmented reality experience that may be suitable for providing a surgeon with appropriate information that may be helpful to reference during surgery, either in tracking mode or in non-tracking mode.

Figure 10:
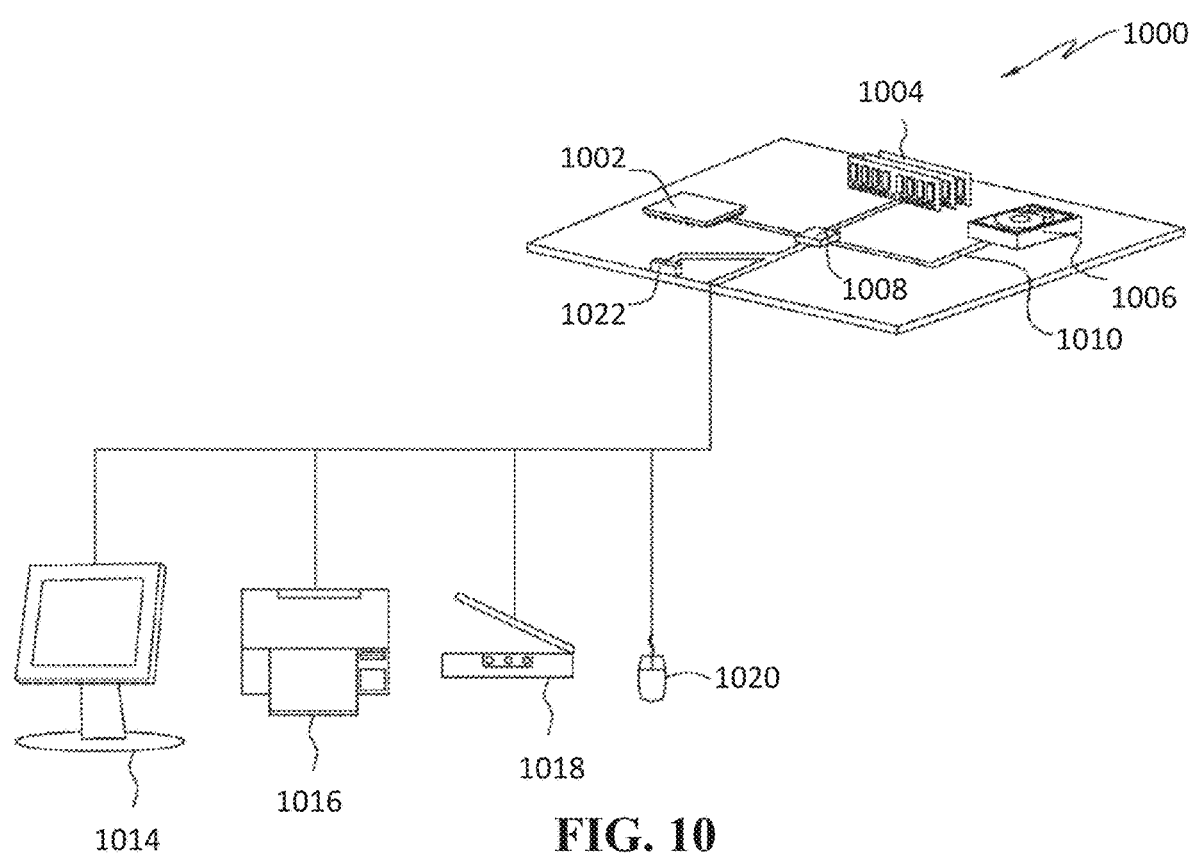
FIG. 10 is a schematic diagram of an example computer for implementing the example ARS computing system of FIG. 4.

FIG. 10 is a schematic diagram of an example computer 1000 for implementing the example AR computing system 412 of FIG. 4. The example computer 1000 is intended to represent various forms of digital computers, including laptops, desktops, handheld computers, tablet computers, smartphones, servers, and other similar types of computing devices. Computer 1000 includes a processor 1002, memory 1004, a storage device 1006, and a communication port 3008, operably connected by an interface 1010 via a bus 1012.

Processor 1002 processes instructions, via memory 1004, for execution within computer 1000. In an example embodiment, multiple processors along with multiple memories may be used.

Memory 1004 may be volatile memory or non-volatile memory. Memory 1004 may be a computer-readable medium, such as a magnetic disk or optical disk. Storage device 1006 may be a computer-readable medium, such as floppy disk devices, a hard disk device, optical disk device, a tape device, a flash memory, phase change memory, or other similar solid state memory device, or an array of devices, including devices in a storage area network of other configurations. A computer program product can be tangibly embodied in a computer readable medium such as memory 1004 or storage device 1006.

Computer 1000 can be coupled to one or more input and output devices such as a display 1014, a printer 1016, a scanner 1018, and a mouse 1020.

While example systems, methods, and so on, have been illustrated by describing examples, and while the examples have been described in considerable detail, it is not the intention to restrict or in any way limit the scope of the appended claims to such detail. It is, of course, not possible to describe every conceivable combination of components or methodologies for purposes of describing the systems, methods, and so on, described herein. Additional advantages and modifications will readily appear to those skilled in the art. Therefore, the invention is not limited to the specific details, and illustrative examples shown or described. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

Many other example embodiments of the invention can be provided through various combinations of the above described features. Although the invention has been described hereinabove using specific examples and embodiments, it will be understood by those skilled in the art that various alternatives may be used and equivalents may be substituted for elements and/or steps described herein, without necessarily deviating from the intended scope of the invention. Modifications may be necessary to adapt the invention to a particular situation or to particular needs without departing from the intended scope of the invention. It is intended that the invention not be limited to the particular implementations and embodiments described herein, but that the claims be given their broadest reasonable interpretation to cover all novel and non-obvious embodiments, literal or equivalent, disclosed or not, covered thereby.

What is claimed is:

1. An augmented reality surgical system comprising:
    a head mounted display configured to provide an optical view of a patient to a user and to inject received data content over top of the optical view to form an augmented reality view of the patient during a medical procedure;
    a model database configured to store model data of tissue and/or organs of the patient generated from previously captured images of actual tissue and/or organs of the patient taken in advance of the medical procedure; and
    an augmented reality computing system comprising one or more processors, one or more computer-readable tangible storage devices, and program instructions stored on at least one of the one or more storage devices for execution by at least one of the one or more processors to perform a method comprising of the steps of:
        tracking a viewing direction of a user wearing the head mounted display;
        tracking a position and/or location of the user wearing the head mounted display as the user changes position relative to the patient;
        tracking a viewing direction of the user using the head mounted display;
        providing an optical view of the patient based on the tracked location and position of the user provided by the tracking mode, wherein said optical view of the patient is updated as the tracking mode updates the position and/or location of the user relative to the patient;
        retrieving at least a portion of said model data from the model database to generate a three-dimensional simulated view of internal tissues of the patient based on both the tracked viewing direction of the user and the tracked location and/or position of the user relative to the patient, wherein said simulated view of internal tissues is updated as the tracked viewing direction of the user changes and is also updated as the tracked position and/or location of the user relative to the patient changes, such that generated three-dimensional simulated view shows internal tissues of the patient as if the user had visual access to those tissues of the patient based on both the user's tracked viewing direction and the user's tracked position and location;
        using the generated simulated view as data content to display to the user using the head mounted display the generated simulated view over top of the optical view associated with the tracked viewing direction and the tracked position and/or location.

2. The system of claim 1, further comprising the step of utilizing a live video stream for generating said augmented reality view.

3. The system of claim 1, wherein the model data comprises a SNAP 3D patient model.

4. The system of claim 1, wherein said model data further comprises a patient health record for displaying to the user.

5. The system of claim 1, further comprising an input interface for receiving a request to cycle through a plurality of different data content options for the user to select at least one of the data content options to be utilized in generating the augmented reality view of the patient.

6. The system of claim 1, wherein the head mounted display comprises internal tracking means configured to determine the position of the user and also to determine the viewing direction of the user relative to the patient.

7. The system of claim 1, wherein said computing system is further configured to perform said method further comprising the step of using the viewing direction and position automatically and in real-time aligning the three-dimensional simulated view of the patient with the optical view of the patient for forming the augmented reality view of the patient.

8. The system of claim 1, further comprising a tracking camera, wherein said system is configured to use said tracking camera to recognize relative markers on the patient for tracking the position and location of the user relative to the patent.

9. The system of claim 8, wherein said system is configured to also use said tracking camera to recognize the relative markers on the patient for tracking the direction of view of the user relative to the patient.

10. The system of claim 1, wherein said method further comprising the step of tracking a position of one or more hands or a tool, or a combination thereof, that are being used for performing a procedure on the patient, said tracking step generating data used generating said augmented view.

11. An augmented reality surgical system comprising:
a head mounted display configured to provide an optical view of a patient to a user and to inject received data content over top of the optical view to form an augmented reality view of the patient during a medical procedure;
a model database configured to store model data of tissue and/or organs of the patient generated from previously captured images of actual tissue and/or organs of the patient taken in advance of the medical procedure;
a camera for generating a live video feed; and
an augmented reality computing system comprising one or more processors, one or more computer-readable tangible storage devices, and program instructions stored on at least one of the one or more storage devices for execution by at least one of the one or more processors to perform a method comprising of the steps of:
tracking a viewing direction of a user wearing the head mounted display;
tracking a position and/or location of the user wearing the head mounted display as the user changes position relative to the patient;
tracking a viewing direction of the user using the head mounted display;
providing a live optical view of the patient from said live video feed, said live optical view based on the tracked location and/or position and/or the viewing direction of the user, wherein said live optical view of the patient is updated as the viewing direction and/or the position and/or location of the user changes;
retrieving at least a portion of said model data from the model database to generate a three-dimensional simulated view of internal tissues of the patient based on both the tracked viewing direction of the user and the tracked location and/or position of the user provided by the tracking mode, wherein said simulated view of internal tissues is updated as the tracked viewing direction of the user changes and is also updated as the tracked position and/or location of the user relative to the patient changes, such that generated three-dimensional simulated view shows internal tissues of the patient as if the user had visual access to those tissues of the patient based on both the user's tracked viewing direction and the user's tracked position and location;
using the generated simulated view as data content to display to the user using the head mounted display the generated simulated view over top of the live optical view associated with the tracked viewing direction and the tracked position and/or location.

12. The system of claim 11, wherein said model data further comprises a patient health record for displaying to the user.

13. The system of claim 11, further comprising an input interface for receiving a request to cycle through a plurality of different data content options for the user to select at least one of the data content options to be utilized in generating the augmented reality view of the patient.

14. The system of claim 11, wherein the head mounted display comprises internal tracking means configured to determine the position of the user and also to determine the viewing direction of the user relative to the patient.

15. The system of claim 11, further comprising a tracking camera, wherein said system is configured to use said tracking camera to recognize relative markers on the patient for tracking the position and location of the user relative to the patent.

16. The system of claim 15, wherein said system is configured to also use said tracking camera to recognize the relative markers on the patient for tracking the direction of view of the user relative to the patient.

17. The system of claim 11, wherein said method further comprising the step of tracking a position of one or more hands or a tool, or a combination thereof, that are being used for performing a procedure on the patient, said tracking step generating data used generating said augmented view.

18. An augmented reality surgical system comprising:
a head mounted display configured to provide an optical view of a patient to a user and to inject received data content over top of the optical view to form an augmented reality view of the patient during a medical procedure, wherein said head mounted display includes one or more sensors for detecting a viewing direction and position of the user;
a model database configured to store model data of tissue and/or organs of the patient generated from previously captured images of actual tissue and/or organs of the patient taken in advance of the medical procedure;
a camera for generating a live video feed; and
an augmented reality computing system comprising one or more processors, one or more computer-readable tangible storage devices, and program instructions stored on at least one of the one or more storage devices for execution by at least one of the one or more processors to perform a method comprising of the steps of:
using the head mounted display for tracking a viewing direction of a user wearing the head mounted display;
using the head mounted display for tracking a position and/or location of the user wearing the head mounted display as the user changes position relative to the patient;
tracking a viewing direction of the user using the head mounted display;
providing a live optical view of the patient from said live video feed, said live optical view based on the tracked location and/or position and/or the viewing direction of the user, wherein said live optical view of the patient is updated as the viewing direction and/or the position and/or location of the user changes;
retrieving at least a portion of said model data from the model database to generate a three-dimensional simulated view of internal tissues of the patient based on both the tracked viewing direction of the user and the tracked location and/or position of the user provided by the tracking mode, wherein said simulated view of internal tissues is updated as the tracked viewing direction of the user changes and is also updated as the tracked position and/or location of the user relative to the patient changes, such that generated three-dimensional simulated view shows internal tissues of the patient as if the user had visual access to those tissues of the patient based on both the user's tracked viewing direction and the user's tracked position and location;

using the generated simulated view as data content to display to the user using the head mounted display the generated simulated view over top of the live optical view associated with the tracked viewing direction and the tracked position and/or location.

19. The system of claim 18, wherein said system is configured to recognize relative markers on the patient for tracking the position and/or location and the direction of view of the user relative to the patent.

20. The system of claim 18, wherein said method further comprising the step of tracking a position of one or more hands or a tool, or a combination thereof, that are being used for performing a procedure on the patient, said tracking step generating data used generating said augmented view.

\* \* \* \* \*